(12) United States Patent
Gabrilovich

(10) Patent No.: US 12,146,156 B2
(45) Date of Patent: Nov. 19, 2024

(54) USE OF LRP2 AGONISTS FOR GENERATING MYELOID-DERIVED SUPPRESSOR CELLS

(71) Applicant: The Wistar Institute of Anatomy and Biology, Philadelphia, PA (US)

(72) Inventor: Dmitry I. Gabrilovich, Villanova, PA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 0 days.

(21) Appl. No.: 17/623,978

(22) PCT Filed: Jul. 1, 2020

(86) PCT No.: PCT/US2020/040499
§ 371 (c)(1),
(2) Date: Dec. 30, 2021

(87) PCT Pub. No.: WO2021/003272
PCT Pub. Date: Jan. 7, 2021

(65) Prior Publication Data
US 2022/0348869 A1 Nov. 3, 2022

Related U.S. Application Data

(60) Provisional application No. 62/869,922, filed on Jul. 2, 2019.

(51) Int. Cl.
*C12N 5/00* (2006.01)
*A61K 35/14* (2015.01)
*A61P 29/00* (2006.01)
*C12N 5/078* (2010.01)

(52) U.S. Cl.
CPC ............ *C12N 5/0634* (2013.01); *A61K 35/14* (2013.01); *A61P 29/00* (2018.01); *C12N 2500/24* (2013.01); *C12N 2501/22* (2013.01); *C12N 2501/2306* (2013.01); *C12N 2501/385* (2013.01); *C12N 2506/1353* (2013.01); *C12N 2510/00* (2013.01)

(58) Field of Classification Search
CPC ................................................... C12N 5/0634
See application file for complete search history.

(56) References Cited

U.S. PATENT DOCUMENTS

| 7,420,033 B2 | 9/2008 | Varadhachary et al. |
| 2006/0110374 A1 | 5/2006 | Czeiger et al. |
| 2012/0082688 A1* | 4/2012 | Chen et al. ............ A61K 35/32 424/184.1 |
| 2012/0315697 A1 | 12/2012 | Pettit et al. |

FOREIGN PATENT DOCUMENTS

| WO | WO 2008/012563 A2 * | 1/2008 | ............. A61K 31/00 |
| WO | WO 2017/044979 | 3/2017 | |
| WO | WO 2017/139588 A1 * | 8/2017 | ............. C12P 21/00 |

OTHER PUBLICATIONS

He et al. (Jan. 15, 2018) "Transitory presence of myeloid-derived suppressor cells in neonates is critical for control of inflammation" Nature medicine, 24(2), 224-231. (Year: 2018).*
Jie et al. (2017) "Large-scale ex vivo generation of human neutrophils from cord blood CD34+ cells" PLoS One, 12(7), e0180832, 18 pages. (Year: 2017).*
Bronte et al. (2016) "Recommendations for myeloid-derived suppressor cell nomenclature and characterization standards", Nature communications, 7(1), 12150, 10 pages. (Year: 2016).*
Cabezas et al. (2011) "Megalin/LRP2 Expression is Induced by Peroxisome Proliferator-Activated Receptor-Alpha and -Gamma: Implications for PPARs' Roles in Renal Function" PLoS One 6(2): e16794. (Year: 2011).*
Liu et al. (2019) "Lactoferrin-induced myeloid-derived suppressor cell therapy attenuates pathologic inflammatory conditions in newborn mice" The Journal of clinical investigation, 129(10), 4261-4275. (Year: 2019).*
Ammendolia et al., Bovine lactoferrin-derived peptides as novel broad-spectrum inhibitors of influenza virus. Pathog Glob Health. Mar. 2012;106(1):12-9.
Barboza et al., Glycosylation of human milk lactoferrin exhibits dynamic changes during early lactation enhancing its role in pathogenic bacteria-host interactions. Mol Cell Proteomics. Jun. 2012;11(6):M111.015248. Epub Jan. 19, 2012.
Bronte et al., Recommendations for myeloid-derived suppressor cell nomenclature and characterization standards. Nat Commun. Jul. 6, 2016;7:12150.
Dufait et al., Ex vivo generation of myeloid-derived suppressor cells that model the tumor immunosuppressive environment in colorectal cancer. Oncotarget. May 20, 2015;6(14):12369-82.
Fan et al., Interrogating Parkinson's disease LRRK2 kinase pathway activity by assessing Rab10 phosphorylation in human neutrophils. Biochem J. Jan. 2, 2018;475(1):23-44.
Hammerich L., & Tacke, F., Emerging roles of myeloid derived suppressor cells in hepatic inflammation and fibrosis. World J Gastrointest Pathophysiol. Aug. 15, 2015;6(3):43-50.

(Continued)

*Primary Examiner* — Teresa E Knight
*Assistant Examiner* — James Joseph Graber
(74) *Attorney, Agent, or Firm* — Howson & Howson, LLP; Colleen M. Schaller; Richard F. Kane

(57) ABSTRACT

Provided herein are methods of generating MDSCs ex vivo. The methods include culturing blood cells with an LRP2 agonist.

13 Claims, 3 Drawing Sheets

Specification includes a Sequence Listing.

(56) References Cited

OTHER PUBLICATIONS

Hayes et al., Phase I trial of oral talactoferrin alfa in refractory solid tumors. Invest New Drugs. May 2006;24(3):233-40.
He et al., Transitory presence of myeloid-derived suppressor cells in neonates is critical for control of inflammation. Nat Med. Feb. 2018;24(2):224-231. Epub Jan. 15, 2018.
Heideveld et al., CD14+ cells from peripheral blood positively regulate hematopoietic stem and progenitor cell survival resulting in increased erythroid yield. Haematologica. Nov. 2015;100(11):1396-406. Epub Aug. 20, 2015.
Hofman et al., Increased *Escherichia coli* phagocytosis in neutrophils that have transmigrated across a cultured intestinal epithelium. Infect Immun. Feb. 2000;68(2):449-55.
Jie et al., Large-scale ex vivo generation of human neutrophils from cord blood CD34+ cells. PLoS One. Jul. 11, 2017;12(7):e0180832.
King et al., A double-blind, placebo-controlled, pilot study of bovine lactoferrin supplementation in bottle-fed infants. J Pediatr Gastroenterol Nutr. Feb. 2007;44(2):245-51.
Kuhns et al., Isolation and Functional Analysis of Human Neutrophils. Curr Protoc Immunol. Nov. 2, 2015;111:7.23.1-7.23.16.
Li et al., A critical concentration of neutrophils is required for effective bacterial killing in suspension. Proc Natl Acad Sci U S A. Jun. 11, 2002;99(12):8289-94.
Liu et al., Lactoferrin-induced myeloid-derived suppressor cell therapy attenuates pathologic inflammatory conditions in newborn mice. J Clin Invest. Oct. 1, 2019;129(10):4261-4275.
Lyons et al., The hidden structure of overimitation. Proc Natl Acad Sci U S A. Dec. 11, 2007;104(50):19751-6. doi: 10.1073/pnas.0704452104. Epub Dec. 4, 2007.
Mandle et al., Infection of human CD34+ progenitor cells with Bartonella henselae results in intraerythrocytic presence of B. henselae. Blood. Aug. 15, 2005;106(4):1215-22. doi: 10.1182/blood-2004-12-4670. Epub Apr. 28, 2005.
Montagne et al., Changes in lactoferrin and lysozyme levels in human milk during the first twelve weeks of lactation. Adv Exp Med Biol. 2001;501:241-7.
Montagne et al., Immunological and nutritional composition of human milk in relation to prematurity and mother's parity during the first 2 weeks of lactation. J Pediatr Gastroenterol Nutr. Jul. 1999;29(1):75-80.
Mueller et al., Efficacy and tolerability of oral lactoferrin supplementation in mild to moderate acne vulgaris: an exploratory study. Curr Med Res Opin. Apr. 2011;27(4):793-7. Epub Feb. 8, 2011.
Mühlebach et al., Stable transduction of primary human monocytes by simian lentiviral vector PBj. Mol Ther. Dec. 2005;12(6):1206-16.Epub Sep. 16, 2005.
Ochoa et al., Impact of lactoferrin supplementation on growth and prevalence of Giardia colonization in children. Clin Infect Dis. Jun. 15, 2008;46(12):1881-3.
Ochoa, T. J. and Cleary, T. G., Effect of lactoferrin on enteric pathogens. Biochimie. Jan. 2009;91(1):30-4. Epub Apr. 18, 2008.
Oh et al., Neutrophil isolation protocol. J Vis Exp. Jul. 23, 2008;(17):745.
Parikh et al., Randomized, double-blind, placebo-controlled phase II study of single-agent oral talactoferrin in patients with locally advanced or metastatic nonsmall-cell lung cancer that progressed after chemotherapy. J Clin Oncol. Nov. 1, 2011;29(31):4129-36. Epub Oct. 3, 2011.
Repnik et al., Simple and cost-effective isolation of monocytes from buffy coats. J Immunol Methods. Jul. 2003;278(1-2):283-92.
Sendo et al., Myeloid-derived suppressor cells in non-neoplastic inflamed organs. Inflamm Regen. Sep. 17, 2018;38:19.
Shi et al., Myeloid-derived suppressor cell function is diminished in aspirintriggered allergic airway hyperresponsiveness in mice. J Allergy Clin Immunol. Nov. 2014;134(5):1163-74.e16. Epub Jun. 17, 2014.
Steijns, J., & Hooijdonk, A.C., Occurrence, structure, biochemical properties and technological characteristics of lactoferrin. Br J Nutr. Nov. 2000;84 Suppl 1:S11-7.
Zavaleta et al., Efficacy of rice-based oral rehydration solution containing recombinant human lactoferrin and lysozyme in Peruvian children with acute diarrhea. J Pediatr Gastroenterol Nutr. Feb. 2007;44(2):258-64.
Zhang et al., Human lactoferrin in the milk of transgenic mice increases intestinal growth in ten-day-old suckling neonates. Adv Exp Med Biol. 2001;501:107-13.
International Search Report and Written Opinion dated Sep. 11, 2020 issued in corresponding International Patent Application No. PCT/US2020/040499.

\* cited by examiner

SEQUENCE LISTING

<160> NUMBER OF SEQ ID NOS: 2

<210> SEQ ID NO 1
<211> LENGTH: 4655
<212> TYPE: PRT
<213> ORGANISM: Homo sapiens

<400> SEQUENCE: 1

```
Met Asp Arg Gly Pro Ala Ala Val Ala Cys Thr Leu Leu Ala Leu
1               5                   10                  15

Val Ala Cys Leu Ala Pro Ala Ser Gly Gln Glu Cys Asp Ser Ala His
            20                  25                  30

Phe Arg Cys Gly Ser Gly His Cys Ile Pro Ala Asp Trp Arg Cys Asp
            35                  40                  45

Gly Thr Lys Asp Cys Ser Asp Ala Asp Glu Ile Gly Cys Ala Val
        50                  55                  60

Val Thr Cys Gln Gln Gly Tyr Phe Lys Cys Gln Ser Glu Gly Gln Cys
65                  70                  75                  80

Ile Pro Asn Ser Trp Val Cys Asp Gln Asp Gln Asp Cys Asp Asp Gly
                85                  90                  95

Ser Asp Glu Arg Gln Asp Cys Ser Gln Ser Thr Cys Ser Ser His Gln
                100                 105                 110

Ile Thr Cys Ser Asn Gly Gln Cys Ile Pro Ser Glu Tyr Arg Cys Asp
                115                 120                 125

His Val Arg Asp Cys Pro Asp Gly Ala Asp Glu Asn Asp Cys Gln Tyr
                130                 135                 140

Pro Thr Cys Glu Gln Leu Thr Cys Asp Asn Gly Ala Cys Tyr Asn Thr
145                 150                 155                 160

Ser Gln Lys Cys Asp Trp Lys Val Asp Cys Arg Asp Ser Ser Asp Glu
                165                 170                 175

Ile Asn Cys Thr Glu Ile Cys Leu His Asn Glu Phe Ser Cys Gly Asn
                180                 185                 190

Gly Glu Cys Ile Pro Arg Ala Tyr Val Cys Asp His Asp Asn Asp Cys
                195                 200                 205

Gln Asp Gly Ser Asp Glu His Ala Cys Asn Tyr Pro Thr Cys Gly Gly
                210                 215                 220

Tyr Gln Phe Thr Cys Pro Ser Gly Arg Cys Ile Tyr Gln Asn Trp Val
225                 230                 235                 240

Cys Asp Gly Glu Asp Asp Cys Lys Asp Asn Gly Asp Glu Asp Gly Cys
                245                 250                 255

Glu Ser Gly Pro His Asp Val His Lys Cys Ser Pro Arg Glu Trp Ser
                260                 265                 270

Cys Pro Glu Ser Gly Arg Cys Ile Ser Ile Tyr Lys Val Cys Asp Gly
                275                 280                 285

Ile Leu Asp Cys Pro Gly Arg Glu Asp Glu Asn Thr Ser Thr Gly
                290                 295                 300

Lys Tyr Cys Ser Met Thr Leu Cys Ser Ala Leu Asn Cys Gln Tyr Gln
305                 310                 315                 320

Cys His Glu Thr Pro Tyr Gly Gly Ala Cys Phe Cys Pro Pro Gly Tyr
                325                 330                 335

Ile Ile Asn His Asn Asp Ser Arg Thr Cys Val Glu Phe Asp Asp Cys
                340                 345                 350

Gln Ile Trp Gly Ile Cys Asp Gln Lys Cys Glu Ser Arg Pro Gly Arg
                355                 360                 365
```

-continued

```
His Leu Cys His Cys Glu Glu Gly Tyr Ile Leu Glu Arg Gly Gln Tyr
    370                 375                 380

Cys Lys Ala Asn Asp Ser Phe Gly Glu Ala Ser Ile Ile Phe Ser Asn
385                 390                 395                 400

Gly Arg Asp Leu Leu Ile Gly Asp Ile His Gly Arg Ser Phe Arg Ile
                405                 410                 415

Leu Val Glu Ser Gln Asn Arg Gly Val Ala Val Gly Val Ala Phe His
            420                 425                 430

Tyr His Leu Gln Arg Val Phe Trp Thr Asp Thr Val Gln Asn Lys Val
        435                 440                 445

Phe Ser Val Asp Ile Asn Gly Leu Asn Ile Gln Glu Val Leu Asn Val
450                 455                 460

Ser Val Glu Thr Pro Glu Asn Leu Ala Val Asp Trp Val Asn Asn Lys
465                 470                 475                 480

Ile Tyr Leu Val Glu Thr Lys Val Asn Arg Ile Asp Met Val Asn Leu
                485                 490                 495

Asp Gly Ser Tyr Arg Val Thr Leu Ile Thr Glu Asn Leu Gly His Pro
            500                 505                 510

Arg Gly Ile Ala Val Asp Pro Thr Val Gly Tyr Leu Phe Phe Ser Asp
        515                 520                 525

Trp Glu Ser Leu Ser Gly Glu Pro Lys Leu Glu Arg Ala Phe Met Asp
530                 535                 540

Gly Ser Asn Arg Lys Asp Leu Val Lys Thr Lys Leu Gly Trp Pro Ala
545                 550                 555                 560

Gly Val Thr Leu Asp Met Ile Ser Lys Arg Val Tyr Trp Val Asp Ser
                565                 570                 575

Arg Phe Asp Tyr Ile Glu Thr Val Thr Tyr Asp Gly Ile Gln Arg Lys
            580                 585                 590

Thr Val Val His Gly Gly Ser Leu Ile Pro His Pro Phe Gly Val Ser
        595                 600                 605

Leu Phe Glu Gly Gln Val Phe Phe Thr Asp Trp Thr Lys Met Ala Val
610                 615                 620

Leu Lys Ala Asn Lys Phe Thr Glu Thr Asn Pro Gln Val Tyr Tyr Gln
625                 630                 635                 640

Ala Ser Leu Arg Pro Tyr Gly Val Thr Val Tyr His Ser Leu Arg Gln
                645                 650                 655

Pro Tyr Ala Thr Asn Pro Cys Lys Asp Asn Asn Gly Gly Cys Glu Gln
            660                 665                 670

Val Cys Val Leu Ser His Arg Thr Asp Asn Asp Gly Leu Gly Phe Arg
        675                 680                 685

Cys Lys Cys Thr Phe Gly Phe Gln Leu Asp Thr Asp Glu Arg His Cys
690                 695                 700

Ile Ala Val Gln Asn Phe Leu Ile Phe Ser Ser Gln Val Ala Ile Arg
705                 710                 715                 720

Gly Ile Pro Phe Thr Leu Ser Thr Gln Glu Asp Val Met Val Pro Val
                725                 730                 735

Ser Gly Asn Pro Ser Phe Phe Val Gly Ile Asp Phe Asp Ala Gln Asp
            740                 745                 750

Ser Thr Ile Phe Phe Ser Asp Met Ser Lys His Met Ile Phe Lys Gln
        755                 760                 765

Lys Ile Asp Gly Thr Gly Arg Glu Ile Leu Ala Ala Asn Arg Val Glu
770                 775                 780

Asn Val Glu Ser Leu Ala Phe Asp Trp Ile Ser Lys Asn Leu Tyr Trp
```

-continued

```
                785                 790                 795                 800
Thr Asp Ser His Tyr Lys Ser Ile Ser Val Met Arg Leu Ala Asp Lys
                805                 810                 815
Thr Arg Arg Thr Val Val Gln Tyr Leu Asn Asn Pro Arg Ser Val Val
                820                 825                 830
Val His Pro Phe Ala Gly Tyr Leu Phe Phe Thr Asp Trp Phe Arg Pro
                835                 840                 845
Ala Lys Ile Met Arg Ala Trp Ser Asp Gly Ser His Leu Leu Pro Val
    850                 855                 860
Ile Asn Thr Thr Leu Gly Trp Pro Asn Gly Leu Ala Ile Asp Trp Ala
865                 870                 875                 880
Ala Ser Arg Leu Tyr Trp Val Asp Ala Tyr Phe Asp Lys Ile Glu His
                885                 890                 895
Ser Thr Phe Asp Gly Leu Asp Arg Arg Arg Leu Gly His Ile Glu Gln
                900                 905                 910
Met Thr His Pro Phe Gly Leu Ala Ile Phe Gly Glu His Leu Phe Phe
                915                 920                 925
Thr Asp Trp Arg Leu Gly Ala Ile Ile Arg Val Arg Lys Ala Asp Gly
    930                 935                 940
Gly Glu Met Thr Val Ile Arg Ser Gly Ile Ala Tyr Ile Leu His Leu
945                 950                 955                 960
Lys Ser Tyr Asp Val Asn Ile Gln Thr Gly Ser Asn Ala Cys Asn Gln
                965                 970                 975
Pro Thr His Pro Asn Gly Asp Cys Ser His Phe Cys Phe Pro Val Pro
                980                 985                 990
Asn Phe Gln Arg Val Cys Gly Cys  Pro Tyr Gly Met Arg  Leu Ala Ser
                995                1000                1005
Asn His  Leu Thr Cys Glu Gly  Asp Pro Thr Asn Glu  Pro Pro Thr
        1010                1015                1020
Glu Gln  Cys Gly Leu Phe Ser  Phe Pro Cys Lys Asn  Gly Arg Cys
        1025                1030                1035
Val Pro  Asn Tyr Tyr Leu Cys  Asp Gly Val Asp Asp  Cys His Asp
        1040                1045                1050
Asn Ser  Asp Glu Gln Leu Cys  Gly Thr Leu Asn Asn  Thr Cys Ser
        1055                1060                1065
Ser Ser  Ala Phe Thr Cys Gly  His Gly Glu Cys Ile  Pro Ala His
        1070                1075                1080
Trp Arg  Cys Asp Lys Arg Asn  Asp Cys Val Asp Gly  Ser Asp Glu
        1085                1090                1095
His Asn  Cys Pro Thr His Ala  Pro Ala Ser Cys Leu  Asp Thr Gln
        1100                1105                1110
Tyr Thr  Cys Asp Asn His Gln  Cys Ile Ser Lys Asn  Trp Val Cys
        1115                1120                1125
Asp Thr  Asp Asn Asp Cys Gly  Asp Gly Ser Asp Glu  Lys Asn Cys
        1130                1135                1140
Asn Ser  Thr Glu Thr Cys Gln  Pro Ser Gln Phe Asn  Cys Pro Asn
        1145                1150                1155
His Arg  Cys Ile Asp Leu Ser  Phe Val Cys Asp Gly  Asp Lys Asp
        1160                1165                1170
Cys Val  Asp Gly Ser Asp Glu  Val Gly Cys Val Leu  Asn Cys Thr
        1175                1180                1185
Ala Ser  Gln Phe Lys Cys Ala  Ser Gly Asp Lys Cys  Ile Gly Val
        1190                1195                1200
```

-continued

```
Thr Asn Arg Cys Asp Gly Val Phe Asp Cys Ser Asp Asn Ser Asp
1205                1210                1215

Glu Ala Gly Cys Pro Thr Arg Pro Pro Gly Met Cys His Ser Asp
1220                1225                1230

Glu Phe Gln Cys Gln Glu Asp Gly Ile Cys Ile Pro Asn Phe Trp
1235                1240                1245

Glu Cys Asp Gly His Pro Asp Cys Leu Tyr Gly Ser Asp Glu His
1250                1255                1260

Asn Ala Cys Val Pro Lys Thr Cys Pro Ser Ser Tyr Phe His Cys
1265                1270                1275

Asp Asn Gly Asn Cys Ile His Arg Ala Trp Leu Cys Asp Arg Asp
1280                1285                1290

Asn Asp Cys Gly Asp Met Ser Asp Glu Lys Asp Cys Pro Thr Gln
1295                1300                1305

Pro Phe Arg Cys Pro Ser Trp Gln Trp Gln Cys Leu Gly His Asn
1310                1315                1320

Ile Cys Val Asn Leu Ser Val Val Cys Asp Gly Ile Phe Asp Cys
1325                1330                1335

Pro Asn Gly Thr Asp Glu Ser Pro Leu Cys Asn Gly Asn Ser Cys
1340                1345                1350

Ser Asp Phe Asn Gly Gly Cys Thr His Glu Cys Val Gln Glu Pro
1355                1360                1365

Phe Gly Ala Lys Cys Leu Cys Pro Leu Gly Phe Leu Leu Ala Asn
1370                1375                1380

Asp Ser Lys Thr Cys Glu Asp Ile Asp Glu Cys Asp Ile Leu Gly
1385                1390                1395

Ser Cys Ser Gln His Cys Tyr Asn Met Arg Gly Ser Phe Arg Cys
1400                1405                1410

Ser Cys Asp Thr Gly Tyr Met Leu Glu Ser Asp Gly Arg Thr Cys
1415                1420                1425

Lys Val Thr Ala Ser Glu Ser Leu Leu Leu Leu Val Ala Ser Gln
1430                1435                1440

Asn Lys Ile Ile Ala Asp Ser Val Thr Ser Gln Val His Asn Ile
1445                1450                1455

Tyr Ser Leu Val Glu Asn Gly Ser Tyr Ile Val Ala Val Asp Phe
1460                1465                1470

Asp Ser Ile Ser Gly Arg Ile Phe Trp Ser Asp Ala Thr Gln Gly
1475                1480                1485

Lys Thr Trp Ser Ala Phe Gln Asn Gly Thr Asp Arg Arg Val Val
1490                1495                1500

Phe Asp Ser Ser Ile Ile Leu Thr Glu Thr Ile Ala Ile Asp Trp
1505                1510                1515

Val Gly Arg Asn Leu Tyr Trp Thr Asp Tyr Ala Leu Glu Thr Ile
1520                1525                1530

Glu Val Ser Lys Ile Asp Gly Ser His Arg Thr Val Leu Ile Ser
1535                1540                1545

Lys Asn Leu Thr Asn Pro Arg Gly Leu Ala Leu Asp Pro Arg Met
1550                1555                1560

Asn Glu His Leu Leu Phe Trp Ser Asp Trp Gly His His Pro Arg
1565                1570                1575

Ile Glu Arg Ala Ser Met Asp Gly Ser Met Arg Thr Val Ile Val
1580                1585                1590
```

```
Gln Asp Lys Ile Phe Trp Pro Cys Gly Leu Thr Ile Asp Tyr Pro
1595                1600                1605

Asn Arg Leu Leu Tyr Phe Met Asp Ser Tyr Leu Asp Tyr Met Asp
1610                1615                1620

Phe Cys Asp Tyr Asn Gly His His Arg Arg Gln Val Ile Ala Ser
1625                1630                1635

Asp Leu Ile Ile Arg His Pro Tyr Ala Leu Thr Leu Phe Glu Asp
1640                1645                1650

Ser Val Tyr Trp Thr Asp Arg Ala Thr Arg Arg Val Met Arg Ala
1655                1660                1665

Asn Lys Trp His Gly Gly Asn Gln Ser Val Val Met Tyr Asn Ile
1670                1675                1680

Gln Trp Pro Leu Gly Ile Val Ala Val His Pro Ser Lys Gln Pro
1685                1690                1695

Asn Ser Val Asn Pro Cys Ala Phe Ser Arg Cys Ser His Leu Cys
1700                1705                1710

Leu Leu Ser Ser Gln Gly Pro His Phe Tyr Ser Cys Val Cys Pro
1715                1720                1725

Ser Gly Trp Ser Leu Ser Pro Asp Leu Leu Asn Cys Leu Arg Asp
1730                1735                1740

Asp Gln Pro Phe Leu Ile Thr Val Arg Gln His Ile Ile Phe Gly
1745                1750                1755

Ile Ser Leu Asn Pro Glu Val Lys Ser Asn Asp Ala Met Val Pro
1760                1765                1770

Ile Ala Gly Ile Gln Asn Gly Leu Asp Val Glu Phe Asp Asp Ala
1775                1780                1785

Glu Gln Tyr Ile Tyr Trp Val Glu Asn Pro Gly Glu Ile His Arg
1790                1795                1800

Val Lys Thr Asp Gly Thr Asn Arg Thr Val Phe Ala Ser Ile Ser
1805                1810                1815

Met Val Gly Pro Ser Met Asn Leu Ala Leu Asp Trp Ile Ser Arg
1820                1825                1830

Asn Leu Tyr Ser Thr Asn Pro Arg Thr Gln Ser Ile Glu Val Leu
1835                1840                1845

Thr Leu His Gly Asp Ile Arg Tyr Arg Lys Thr Leu Ile Ala Asn
1850                1855                1860

Asp Gly Thr Ala Leu Gly Val Gly Phe Pro Ile Gly Ile Thr Val
1865                1870                1875

Asp Pro Ala Arg Gly Lys Leu Tyr Trp Ser Asp Gln Gly Thr Asp
1880                1885                1890

Ser Gly Val Pro Ala Lys Ile Ala Ser Ala Asn Met Asp Gly Thr
1895                1900                1905

Ser Val Lys Thr Leu Phe Thr Gly Asn Leu Glu His Leu Glu Cys
1910                1915                1920

Val Thr Leu Asp Ile Glu Glu Gln Lys Leu Tyr Trp Ala Val Thr
1925                1930                1935

Gly Arg Gly Val Ile Glu Arg Gly Asn Val Asp Gly Thr Asp Arg
1940                1945                1950

Met Ile Leu Val His Gln Leu Ser His Pro Trp Gly Ile Ala Val
1955                1960                1965

His Asp Ser Phe Leu Tyr Tyr Thr Asp Glu Gln Tyr Glu Val Ile
1970                1975                1980

Glu Arg Val Asp Lys Ala Thr Gly Ala Asn Lys Ile Val Leu Arg
```

-continued

```
            1985                1990                1995
Asp Asn Val Pro Asn Leu Arg Gly Leu Gln Val Tyr His Arg Arg
            2000                2005                2010

Asn Ala Ala Glu Ser Ser Asn Gly Cys Ser Asn Asn Met Asn Ala
            2015                2020                2025

Cys Gln Gln Ile Cys Leu Pro Val Pro Gly Gly Leu Phe Ser Cys
            2030                2035                2040

Ala Cys Ala Thr Gly Phe Lys Leu Asn Pro Asp Asn Arg Ser Cys
            2045                2050                2055

Ser Pro Tyr Asn Ser Phe Ile Val Val Ser Met Leu Ser Ala Ile
            2060                2065                2070

Arg Gly Phe Ser Leu Glu Leu Ser Asp His Ser Glu Thr Met Val
            2075                2080                2085

Pro Val Ala Gly Gln Gly Arg Asn Ala Leu His Val Asp Val Asp
            2090                2095                2100

Val Ser Ser Gly Phe Ile Tyr Trp Cys Asp Phe Ser Ser Ser Val
            2105                2110                2115

Ala Ser Asp Asn Ala Ile Arg Arg Ile Lys Pro Asp Gly Ser Ser
            2120                2125                2130

Leu Met Asn Ile Val Thr His Gly Ile Gly Glu Asn Gly Val Arg
            2135                2140                2145

Gly Ile Ala Val Asp Trp Val Ala Gly Asn Leu Tyr Phe Thr Asn
            2150                2155                2160

Ala Phe Val Ser Glu Thr Leu Ile Glu Val Leu Arg Ile Asn Thr
            2165                2170                2175

Thr Tyr Arg Arg Val Leu Leu Lys Val Thr Val Asp Met Pro Arg
            2180                2185                2190

His Ile Val Val Asp Pro Lys Asn Arg Tyr Leu Phe Trp Ala Asp
            2195                2200                2205

Tyr Gly Gln Arg Pro Lys Ile Glu Arg Ser Phe Leu Asp Cys Thr
            2210                2215                2220

Asn Arg Thr Val Leu Val Ser Glu Gly Ile Val Thr Pro Arg Gly
            2225                2230                2235

Leu Ala Val Asp Arg Ser Asp Gly Tyr Val Tyr Trp Val Asp Asp
            2240                2245                2250

Ser Leu Asp Ile Ile Ala Arg Ile Arg Ile Asn Gly Glu Asn Ser
            2255                2260                2265

Glu Val Ile Arg Tyr Gly Ser Arg Tyr Pro Thr Pro Tyr Gly Ile
            2270                2275                2280

Thr Val Phe Glu Asn Ser Ile Ile Trp Val Asp Arg Asn Leu Lys
            2285                2290                2295

Lys Ile Phe Gln Ala Ser Lys Glu Pro Glu Asn Thr Glu Pro Pro
            2300                2305                2310

Thr Val Ile Arg Asp Asn Ile Asn Trp Leu Arg Asp Val Thr Ile
            2315                2320                2325

Phe Asp Lys Gln Val Gln Pro Arg Ser Pro Ala Glu Val Asn Asn
            2330                2335                2340

Asn Pro Cys Leu Glu Asn Asn Gly Gly Cys Ser His Leu Cys Phe
            2345                2350                2355

Ala Leu Pro Gly Leu His Thr Pro Lys Cys Asp Cys Ala Phe Gly
            2360                2365                2370

Thr Leu Gln Ser Asp Gly Lys Asn Cys Ala Ile Ser Thr Glu Asn
            2375                2380                2385
```

```
Phe Leu Ile Phe Ala Leu Ser Asn Ser Leu Arg Ser Leu His Leu
    2390            2395                2400

Asp Pro Glu Asn His Ser Pro Pro Phe Gln Thr Ile Asn Val Glu
    2405            2410                2415

Arg Thr Val Met Ser Leu Asp Tyr Asp Ser Val Ser Asp Arg Ile
    2420            2425                2430

Tyr Phe Thr Gln Asn Leu Ala Ser Gly Val Gly Gln Ile Ser Tyr
    2435            2440                2445

Ala Thr Leu Ser Ser Gly Ile His Thr Pro Thr Val Ile Ala Ser
    2450            2455                2460

Gly Ile Gly Thr Ala Asp Gly Ile Ala Phe Asp Trp Ile Thr Arg
    2465            2470                2475

Arg Ile Tyr Tyr Ser Asp Tyr Leu Asn Gln Met Ile Asn Ser Met
    2480            2485                2490

Ala Glu Asp Gly Ser Asn Arg Thr Val Ile Ala Arg Val Pro Lys
    2495            2500                2505

Pro Arg Ala Ile Val Leu Asp Pro Cys Gln Gly Tyr Leu Tyr Trp
    2510            2515                2520

Ala Asp Trp Asp Thr His Ala Lys Ile Glu Arg Ala Thr Leu Gly
    2525            2530                2535

Gly Asn Phe Arg Val Pro Ile Val Asn Ser Ser Leu Val Met Pro
    2540            2545                2550

Ser Gly Leu Thr Leu Asp Tyr Glu Glu Asp Leu Leu Tyr Trp Val
    2555            2560                2565

Asp Ala Ser Leu Gln Arg Ile Glu Arg Ser Thr Leu Thr Gly Val
    2570            2575                2580

Asp Arg Glu Val Ile Val Asn Ala Ala Val His Ala Phe Gly Leu
    2585            2590                2595

Thr Leu Tyr Gly Gln Tyr Ile Tyr Trp Thr Asp Leu Tyr Thr Gln
    2600            2605                2610

Arg Ile Tyr Arg Ala Asn Lys Tyr Asp Gly Ser Gly Gln Ile Ala
    2615            2620                2625

Met Thr Thr Asn Leu Leu Ser Gln Pro Arg Gly Ile Asn Thr Val
    2630            2635                2640

Val Lys Asn Gln Lys Gln Gln Cys Asn Asn Pro Cys Glu Gln Phe
    2645            2650                2655

Asn Gly Gly Cys Ser His Ile Cys Ala Pro Gly Pro Asn Gly Ala
    2660            2665                2670

Glu Cys Gln Cys Pro His Glu Gly Asn Trp Tyr Leu Ala Asn Asn
    2675            2680                2685

Arg Lys His Cys Ile Val Asp Asn Gly Glu Arg Cys Gly Ala Ser
    2690            2695                2700

Ser Phe Thr Cys Ser Asn Gly Arg Cys Ile Ser Glu Glu Trp Lys
    2705            2710                2715

Cys Asp Asn Asp Asn Asp Cys Gly Asp Gly Ser Asp Glu Met Glu
    2720            2725                2730

Ser Val Cys Ala Leu His Thr Cys Ser Pro Thr Ala Phe Thr Cys
    2735            2740                2745

Ala Asn Gly Arg Cys Val Gln Tyr Ser Tyr Arg Cys Asp Tyr Tyr
    2750            2755                2760

Asn Asp Cys Gly Asp Gly Ser Asp Glu Ala Gly Cys Leu Phe Arg
    2765            2770                2775
```

```
Asp Cys Asn Ala Thr Thr Glu Phe Met Cys Asn Asn Arg Arg Cys
2780                2785                2790

Ile Pro Arg Glu Phe Ile Cys Asn Gly Val Asp Asn Cys His Asp
2795                2800                2805

Asn Asn Thr Ser Asp Glu Lys Asn Cys Pro Asp Arg Thr Cys Gln
2810                2815                2820

Ser Gly Tyr Thr Lys Cys His Asn Ser Asn Ile Cys Ile Pro Arg
2825                2830                2835

Val Tyr Leu Cys Asp Gly Asp Asn Asp Cys Gly Asp Asn Ser Asp
2840                2845                2850

Glu Asn Pro Thr Tyr Cys Thr His Thr Cys Ser Ser Ser Glu
2855                2860                2865

Phe Gln Cys Ala Ser Gly Arg Cys Ile Pro Gln His Trp Tyr Cys
2870                2875                2880

Asp Gln Glu Thr Asp Cys Phe Asp Ala Ser Asp Glu Pro Ala Ser
2885                2890                2895

Cys Gly His Ser Glu Arg Thr Cys Leu Ala Asp Glu Phe Lys Cys
2900                2905                2910

Asp Gly Gly Arg Cys Ile Pro Ser Glu Trp Ile Cys Asp Gly Asp
2915                2920                2925

Asn Asp Cys Gly Asp Met Ser Asp Glu Asp Lys Arg His Gln Cys
2930                2935                2940

Gln Asn Gln Asn Cys Ser Asp Ser Glu Phe Leu Cys Val Asn Asp
2945                2950                2955

Arg Pro Pro Asp Arg Arg Cys Ile Pro Gln Ser Trp Val Cys Asp
2960                2965                2970

Gly Asp Val Asp Cys Thr Asp Gly Tyr Asp Glu Asn Gln Asn Cys
2975                2980                2985

Thr Arg Arg Thr Cys Ser Glu Asn Glu Phe Thr Cys Gly Tyr Gly
2990                2995                3000

Leu Cys Ile Pro Lys Ile Phe Arg Cys Asp Arg His Asn Asp Cys
3005                3010                3015

Gly Asp Tyr Ser Asp Glu Arg Gly Cys Leu Tyr Gln Thr Cys Gln
3020                3025                3030

Gln Asn Gln Phe Thr Cys Gln Asn Gly Arg Cys Ile Ser Lys Thr
3035                3040                3045

Phe Val Cys Asp Glu Asp Asn Asp Cys Gly Asp Gly Ser Asp Glu
3050                3055                3060

Leu Met His Leu Cys His Thr Pro Glu Pro Thr Cys Pro Pro His
3065                3070                3075

Glu Phe Lys Cys Asp Asn Gly Arg Cys Ile Glu Met Met Lys Leu
3080                3085                3090

Cys Asn His Leu Asp Asp Cys Leu Asp Asn Ser Asp Glu Lys Gly
3095                3100                3105

Cys Gly Ile Asn Glu Cys His Asp Pro Ser Ile Ser Gly Cys Asp
3110                3115                3120

His Asn Cys Thr Asp Thr Leu Thr Ser Phe Tyr Cys Ser Cys Arg
3125                3130                3135

Pro Gly Tyr Lys Leu Met Ser Asp Lys Arg Thr Cys Val Asp Ile
3140                3145                3150

Asp Glu Cys Thr Glu Met Pro Phe Val Cys Ser Gln Lys Cys Glu
3155                3160                3165

Asn Val Ile Gly Ser Tyr Ile Cys Lys Cys Ala Pro Gly Tyr Leu
```

```
                3170                3175                3180
Arg Glu Pro Asp Gly Lys Thr Cys Arg Gln Asn Ser Asn Ile Glu
    3185                3190                3195
Pro Tyr Leu Ile Phe Ser Asn Arg Tyr Leu Arg Asn Leu Thr
    3200                3205                3210
Ile Asp Gly Tyr Phe Tyr Ser Leu Ile Leu Glu Gly Leu Asp Asn
    3215                3220                3225
Val Val Ala Leu Asp Phe Asp Arg Val Glu Lys Arg Leu Tyr Trp
    3230                3235                3240
Ile Asp Thr Gln Arg Gln Val Ile Glu Arg Met Phe Leu Asn Lys
    3245                3250                3255
Thr Asn Lys Glu Thr Ile Ile Asn His Arg Leu Pro Ala Ala Glu
    3260                3265                3270
Ser Leu Ala Val Asp Trp Val Ser Arg Lys Leu Tyr Trp Leu Asp
    3275                3280                3285
Ala Arg Leu Asp Gly Leu Phe Val Ser Asp Leu Asn Gly Gly His
    3290                3295                3300
Arg Arg Met Leu Ala Gln His Cys Val Asp Ala Asn Asn Thr Phe
    3305                3310                3315
Cys Phe Asp Asn Pro Arg Gly Leu Ala Leu His Pro Gln Tyr Gly
    3320                3325                3330
Tyr Leu Tyr Trp Ala Asp Trp Gly His Arg Ala Tyr Ile Gly Arg
    3335                3340                3345
Val Gly Met Asp Gly Thr Asn Lys Ser Val Ile Ile Ser Thr Lys
    3350                3355                3360
Leu Glu Trp Pro Asn Gly Ile Thr Ile Asp Tyr Thr Asn Asp Leu
    3365                3370                3375
Leu Tyr Trp Ala Asp Ala His Leu Gly Tyr Ile Glu Tyr Ser Asp
    3380                3385                3390
Leu Glu Gly His His Arg His Thr Val Tyr Asp Gly Ala Leu Pro
    3395                3400                3405
His Pro Phe Ala Ile Thr Ile Phe Glu Asp Thr Ile Tyr Trp Thr
    3410                3415                3420
Asp Trp Asn Thr Arg Thr Val Glu Lys Gly Asn Lys Tyr Asp Gly
    3425                3430                3435
Ser Asn Arg Gln Thr Leu Val Asn Thr Thr His Arg Pro Phe Asp
    3440                3445                3450
Ile His Val Tyr His Pro Tyr Arg Gln Pro Ile Val Ser Asn Pro
    3455                3460                3465
Cys Gly Thr Asn Asn Gly Gly Cys Ser His Leu Cys Leu Ile Lys
    3470                3475                3480
Pro Gly Gly Lys Gly Phe Thr Cys Glu Cys Pro Asp Asp Phe Arg
    3485                3490                3495
Thr Leu Gln Leu Ser Gly Ser Thr Tyr Cys Met Pro Met Cys Ser
    3500                3505                3510
Ser Thr Gln Phe Leu Cys Ala Asn Asn Glu Lys Cys Ile Pro Ile
    3515                3520                3525
Trp Trp Lys Cys Asp Gly Gln Lys Asp Cys Ser Asp Gly Ser Asp
    3530                3535                3540
Glu Leu Ala Leu Cys Pro Gln Arg Phe Cys Arg Leu Gly Gln Phe
    3545                3550                3555
Gln Cys Ser Asp Gly Asn Cys Thr Ser Pro Gln Thr Leu Cys Asn
    3560                3565                3570
```

```
Ala His Gln Asn Cys Pro Asp Gly Ser Asp Glu Asp Arg Leu Leu
3575                 3580                3585

Cys Glu Asn His His Cys Asp Ser Asn Glu Trp Gln Cys Ala Asn
    3590                3595                3600

Lys Arg Cys Ile Pro Glu Ser Trp Gln Cys Asp Thr Phe Asn Asp
3605                 3610                3615

Cys Glu Asp Asn Ser Asp Glu Asp Ser Ser His Cys Ala Ser Arg
3620                 3625                3630

Thr Cys Arg Pro Gly Gln Phe Arg Cys Ala Asn Gly Arg Cys Ile
3635                 3640                3645

Pro Gln Ala Trp Lys Cys Asp Val Asp Asn Asp Cys Gly Asp His
3650                 3655                3660

Ser Asp Glu Pro Ile Glu Glu Cys Met Ser Ser Ala His Leu Cys
3665                 3670                3675

Asp Asn Phe Thr Glu Phe Ser Cys Lys Thr Asn Tyr Arg Cys Ile
3680                 3685                3690

Pro Lys Trp Ala Val Cys Asn Gly Val Asp Asp Cys Arg Asp Asn
3695                 3700                3705

Ser Asp Glu Gln Gly Cys Glu Glu Arg Thr Cys His Pro Val Gly
3710                 3715                3720

Asp Phe Arg Cys Lys Asn His His Cys Ile Pro Leu Arg Trp Gln
3725                 3730                3735

Cys Asp Gly Gln Asn Asp Cys Gly Asp Asn Ser Asp Glu Glu Asn
3740                 3745                3750

Cys Ala Pro Arg Glu Cys Thr Glu Ser Glu Phe Arg Cys Val Asn
3755                 3760                3765

Gln Gln Cys Ile Pro Ser Arg Trp Ile Cys Asp His Tyr Asn Asp
3770                 3775                3780

Cys Gly Asp Asn Ser Asp Glu Arg Asp Cys Glu Met Arg Thr Cys
3785                 3790                3795

His Pro Glu Tyr Phe Gln Cys Thr Ser Gly His Cys Val His Ser
3800                 3805                3810

Glu Leu Lys Cys Asp Gly Ser Ala Asp Cys Leu Asp Ala Ser Asp
3815                 3820                3825

Glu Ala Asp Cys Pro Thr Arg Phe Pro Asp Gly Ala Tyr Cys Gln
3830                 3835                3840

Ala Thr Met Phe Glu Cys Lys Asn His Val Cys Ile Pro Pro Tyr
3845                 3850                3855

Trp Lys Cys Asp Gly Asp Asp Cys Gly Asp Gly Ser Asp Glu
3860                 3865                3870

Glu Leu His Leu Cys Leu Asp Val Pro Cys Asn Ser Pro Asn Arg
3875                 3880                3885

Phe Arg Cys Asp Asn Asn Arg Cys Ile Tyr Ser His Glu Val Cys
3890                 3895                3900

Asn Gly Val Asp Asp Cys Gly Asp Gly Thr Asp Glu Thr Glu Glu
3905                 3910                3915

His Cys Arg Lys Pro Thr Pro Lys Pro Cys Thr Glu Tyr Glu Tyr
3920                 3925                3930

Lys Cys Gly Asn Gly His Cys Ile Pro His Asp Asn Val Cys Asp
3935                 3940                3945

Asp Ala Asp Asp Cys Gly Asp Trp Ser Asp Glu Leu Gly Cys Asn
3950                 3955                3960
```

```
Lys Gly Lys Glu Arg Thr Cys Ala Glu Asn Ile Cys Glu Gln Asn
3965                3970                3975

Cys Thr Gln Leu Asn Glu Gly Gly Phe Ile Cys Ser Cys Thr Ala
3980                3985                3990

Gly Phe Glu Thr Asn Val Phe Asp Arg Thr Ser Cys Leu Asp Ile
3995                4000                4005

Asn Glu Cys Glu Gln Phe Gly Thr Cys Pro Gln His Cys Arg Asn
4010                4015                4020

Thr Lys Gly Ser Tyr Glu Cys Val Cys Ala Asp Gly Phe Thr Ser
4025                4030                4035

Met Ser Asp Arg Pro Gly Lys Arg Cys Ala Ala Glu Gly Ser Ser
4040                4045                4050

Pro Leu Leu Leu Leu Pro Asp Asn Val Arg Ile Arg Lys Tyr Asn
4055                4060                4065

Leu Ser Ser Glu Arg Phe Ser Glu Tyr Leu Gln Asp Glu Glu Tyr
4070                4075                4080

Ile Gln Ala Val Asp Tyr Asp Trp Asp Pro Lys Asp Ile Gly Leu
4085                4090                4095

Ser Val Val Tyr Tyr Thr Val Arg Gly Glu Gly Ser Arg Phe Gly
4100                4105                4110

Ala Ile Lys Arg Ala Tyr Ile Pro Asn Phe Glu Ser Gly Arg Asn
4115                4120                4125

Asn Leu Val Gln Glu Val Asp Leu Lys Leu Lys Tyr Val Met Gln
4130                4135                4140

Pro Asp Gly Ile Ala Val Asp Trp Val Gly Arg His Ile Tyr Trp
4145                4150                4155

Ser Asp Val Lys Asn Lys Arg Ile Glu Val Ala Lys Leu Asp Gly
4160                4165                4170

Arg Tyr Arg Lys Trp Leu Ile Ser Thr Asp Leu Asp Gln Pro Ala
4175                4180                4185

Ala Ile Ala Val Asn Pro Lys Leu Gly Leu Met Phe Trp Thr Asp
4190                4195                4200

Trp Gly Lys Glu Pro Lys Ile Glu Ser Ala Trp Met Asn Gly Glu
4205                4210                4215

Asp Arg Asn Ile Leu Val Phe Glu Asp Leu Gly Trp Pro Thr Gly
4220                4225                4230

Leu Ser Ile Asp Tyr Leu Asn Asn Asp Arg Ile Tyr Trp Ser Asp
4235                4240                4245

Phe Lys Glu Asp Val Ile Glu Thr Ile Lys Tyr Asp Gly Thr Asp
4250                4255                4260

Arg Arg Val Ile Ala Lys Glu Ala Met Asn Pro Tyr Ser Leu Asp
4265                4270                4275

Ile Phe Glu Asp Gln Leu Tyr Trp Ile Ser Lys Glu Lys Gly Glu
4280                4285                4290

Val Trp Lys Gln Asn Lys Phe Gly Gln Gly Lys Lys Glu Lys Thr
4295                4300                4305

Leu Val Val Asn Pro Trp Leu Thr Gln Val Arg Ile Phe His Gln
4310                4315                4320

Leu Arg Tyr Asn Lys Ser Val Pro Asn Leu Cys Lys Gln Ile Cys
4325                4330                4335

Ser His Leu Cys Leu Leu Arg Pro Gly Gly Tyr Ser Cys Ala Cys
4340                4345                4350

Pro Gln Gly Ser Ser Phe Ile Glu Gly Ser Thr Thr Glu Cys Asp
```

```
      4355                4360                4365
Ala Ala Ile Glu Leu Pro Ile Asn Leu Pro Pro Cys Arg Cys
      4370                4375                4380

Met His Gly Gly Asn Cys Tyr Phe Asp Glu Thr Asp Leu Pro Lys
      4385                4390                4395

Cys Lys Cys Pro Ser Gly Tyr Thr Gly Lys Tyr Cys Glu Met Ala
      4400                4405                4410

Phe Ser Lys Gly Ile Ser Pro Gly Thr Thr Ala Val Ala Val Leu
      4415                4420                4425

Leu Thr Ile Leu Leu Ile Val Val Ile Gly Ala Leu Ala Ile Ala
      4430                4435                4440

Gly Phe Phe His Tyr Arg Arg Thr Gly Ser Leu Leu Pro Ala Leu
      4445                4450                4455

Pro Lys Leu Pro Ser Leu Ser Ser Leu Val Lys Pro Ser Glu Asn
      4460                4465                4470

Gly Asn Gly Val Thr Phe Arg Ser Gly Ala Asp Leu Asn Met Asp
      4475                4480                4485

Ile Gly Val Ser Gly Phe Gly Pro Glu Thr Ala Ile Asp Arg Ser
      4490                4495                4500

Met Ala Met Ser Glu Asp Phe Val Met Glu Met Gly Lys Gln Pro
      4505                4510                4515

Ile Ile Phe Glu Asn Pro Met Tyr Ser Ala Arg Asp Ser Ala Val
      4520                4525                4530

Lys Val Val Gln Pro Ile Gln Val Thr Val Ser Glu Asn Val Asp
      4535                4540                4545

Asn Lys Asn Tyr Gly Ser Pro Ile Asn Pro Ser Glu Ile Val Pro
      4550                4555                4560

Glu Thr Asn Pro Thr Ser Pro Ala Ala Asp Gly Thr Gln Val Thr
      4565                4570                4575

Lys Trp Asn Leu Phe Lys Arg Lys Ser Lys Gln Thr Thr Asn Phe
      4580                4585                4590

Glu Asn Pro Ile Tyr Ala Gln Met Glu Asn Glu Gln Lys Glu Ser
      4595                4600                4605

Val Ala Ala Thr Pro Pro Pro Ser Pro Ser Leu Pro Ala Lys Pro
      4610                4615                4620

Lys Pro Pro Ser Arg Arg Asp Pro Thr Pro Thr Tyr Ser Ala Thr
      4625                4630                4635

Glu Asp Thr Phe Lys Asp Thr Ala Asn Leu Val Lys Glu Asp Ser
      4640                4645                4650

Glu Val
      4655

<210> SEQ ID NO 2
<211> LENGTH: 13968
<212> TYPE: DNA
<213> ORGANISM: Homo sapiens

<400> SEQUENCE: 2
atggatcgcg ggccggcagc agtggcgtgc acgctgctcc tggctctcgt cgcctgccta      60
gcgccggcca gtggccaaga atgtgacagt gcgcattttc gctgtggaag tgggcattgc     120
atccctgcag actggaggtg tgatgggacc aaagactgtt cagatgacgc ggatgaaatt     180
ggctgcgctg ttgtgacctg ccagcagggc tatttcaagt gccagagtga gggacaatgc     240
atccccaact cctgggtgtg tgaccaagat caagactgtg atgatggctc agatgaacgt     300
```

-continued

```
caagattgct cacaaagtac atgctcaagt catcagataa catgctccaa tggtcagtgt    360
atcccaagtg aatacaggtg cgaccacgtc agagactgcc ccgatggagc tgatgagaat    420
gactgccagt acccaacatg tgagcagctt acttgtgaca atggggcctg ctataacacc    480
agtcagaagt gtgattggaa agttgattgc agggactcct cagatgaaat caactgcact    540
gagatatgct tgcacaatga gttttcatgt ggcaatggag agtgtatccc tcgtgcttat    600
gtctgtgacc atgacaatga ttgccaagac ggcagtgacg aacatgcttg caactatccg    660
acctgcggtg gttaccagtt cacttgcccc agtggccgat gcatttatca aaactgggtt    720
tgtgatggag aagatgactg taaagataat ggagatgaag atggatgtga aagcggtcct    780
catgatgttc ataaatgttc cccaagagaa tggtcttgcc cagagtcggg acgatgcatc    840
tccatttata aagtttgtga tgggatttta gattgcccag aagagaaga tgaaaacaac    900 actagtaccg aaaatactg tagtatgact ctgtgctctg ccttgaactg ccagtaccag    960
tgccatgaga cgccgtatgg aggagcgtgt ttttgtcccc caggttatat catcaaccac    1020
aatgacagcc gtacctgtgt tgagtttgat gattgccaga tatgggaat ttgtgaccag    1080 aagtgtgaaa gccgacctgg ccgtcacctg tgccactgtg aagaagggta tatcttggag    1140
cgtggacagt attgcaaagc taatgattcc tttggcgagg cctccattat cttctccaat    1200
ggtcgggatt tgttaattgg tgatattcat ggaaggagct tccggatcct agtggagtct    1260
cagaatcgtg gagtggccgt gggtgtggct ttccactatc acctgcaaag agttttttgg    1320
acagacaccg tgcaaaataa ggtttttttca gttgacatta atggtttaaa tatccaagag    1380
gttctcaatg tttctgttga accccagag aacctggctg tggactgggt taataataaa    1440
atctatctag tggaaaccaa ggtcaaccgc atagatatgg taaatttgga tggaagctat    1500
cgggttaccc ttataactga aaacttgggg catcctagag aattgccgt ggacccaact    1560 gttggttatt tattttttctc agattgggag agccttctg gggaacctaa gctggaaagg    1620
gcattcatgg atggcagcaa ccgtaaagac ttggtgaaaa caaagctggg atggcctgct    1680
ggggtaactc tggatatgat atcgaagcgt gtttactggg ttgactctcg gtttgattac    1740
attgaaactg taacttatga tggaattcaa aggaagactg tagttcatgg aggctccctc    1800
attcctcatc cctttggagt aagcttattt gaaggtcagg tgttctttac agattggaca    1860
aagatggccg tgctgaaggc aaacaagttc acagagacca acccacaagt gtactaccag    1920
gcttccctga ggccctatgg agtgactgtt taccattccc tcagacagcc ctatgctacc    1980
aatccgtgta aagataacaa tggggctgt gagcaggtct gtgtcctcag ccacagaaca    2040
gataatgatg gtttgggttt ccgttgcaag tgcacattcg gcttccaact ggatacagat    2100
gagcgccact gcattgctgt tcagaatttc ctcatttttt catcccaagt tgctattcgt    2160
gggatcccgt tcaccttgtc tacccaggaa gatgtcatgg ttccagtttc ggggaatcct    2220 tcttttcttttg tcgggattga ttttgacgcc caggacagca ctatcttttt ttcagatatg    2280
tcaaaacaca tgattttttaa gcaaaagatt gatggcacag aagagaaat tctcgcagct    2340 aacagggtgg aaaatgttga aagtttggct tttgattgga tttcaaagaa tctctattgg    2400
acagactctc attacaagag tatcagtgtc atgaggctag ctgataaaac gagacgcaca    2460
gtagttcagt atttaaataa cccacggtcg gtggtagttc atccttttgc cgggtatcta    2520
ttcttcactg attggttccg tcctgctaaa attatgagag catggagtga cggatctcac    2580
ctcttgcctg taataaacac tactcttgga tgcccaatg gcttggccat cgattgggct    2640
```

```
gcttcacgat tgtactgggt agatgcctat tttgataaaa ttgagcacag cacctttgat    2700
ggtttagaca gaagaagact gggccatata gagcagatga cacatccgtt tggacttgcc    2760
atctttggag agcatttatt ttttactgac tggagactgg gtgccattat tcgagtcagg    2820
aaagcagatg gtggagaaat gacagttatc cgaagtggca ttgcttacat actgcatttg    2880
aaatcgtatg atgtcaacat ccagactggt tctaacgcct gtaatcaacc cacgcatcct    2940
aacggtgact gcagccactt ctgcttcccg gtgccaaatt ccagcgagt gtgtgggtgc     3000
ccttatggaa tgaggctggc ttccaatcac ttgacatgcg aggggaccc aaccaatgaa     3060
ccacccacag agcagtgtgg cttatttttcc ttccctgta aaatggcag atgtgtgccc    3120
aattactatc tctgtgatgg agtcgatgat tgtcatgata acagtgatga gcaactatgt   3180
ggcacactta ataatacctg ttcatcttcg gcgttcacct gtggccatgg ggagtgcatt   3240
cctgcacact ggcgctgtga caaacgcaac gactgtgtgg atggcagtga tgagcacaac   3300
tgccccaccc acgcacctgc ttcctgcctt gacacccaat acacctgtga taatcaccag   3360
tgtatctcaa agaactgggt ctgtgacaca gacaatgatt gtgggatgg atctgatgaa    3420
aagaactgca attcgacaga gacatgccaa cctagtcagt ttaattgccc caatcatcga   3480
tgtattgacc tatcgtttgt ctgtgatggt gacaaggatt gtgttgatgg atctgatgag   3540
gttggttgtg tattaaactg tactgcttct caattcaagt gtgccagtgg ggataaatgt   3600
attggcgtca caaatcgttg tgatggtgtt tttgattgca gtgacaactc ggatgaagca   3660
ggctgtccaa ccaggcctcc tggtatgtgc cactcagatg aatttcagtg ccaagaagat   3720
ggtatctgca tcccgaactt ctgggaatgt gatgggcatc cagactgcct ctatggatct   3780
gatgagcaca atgcctgtgt ccccaagact tgcccttcat catatttcca ctgtgacaac   3840
ggaaactgca tccacagggc atggctctgt gatcgggaca atgactgcgg gatatgagt    3900
gatgagaagg actgccctac tcagccctttt cgctgtccta gttggcaatg gcagtgtctt   3960
ggccataaca tctgtgtgaa tctgagtgta gtgtgtgatg gcatctttga ctgccccaat   4020
gggacagatg agtccccact ttgcaatggg aacagctgct cagatttcaa tggtggttgt   4080
actcacgagt gtgttcaaga gccctttggg gctaaatgcc tatgtccatt gggattctta   4140
cttgccaatg attctaagac ctgtgaagac atagatgaat gtgatattct aggctcttgt   4200
agccagcact gttacaatat gagaggttct ttccggtgct cgtgtgatac aggctacatg   4260
ttagaaagtg atgggaggac ttgcaaagtt acagcatctg agagtctgct gttacttgtg   4320
gcaagtcaga acaaaattat tgccgacagt gtcacctccc aggtccacaa tatctattca   4380
ttggtcgaga atggttctta cattgtagct gttgattttg attcaattag tggtcgtatc   4440
ttttggtctg atgcaactca gggtaaaacc tggagtgcgt ttcaaaatgg aacggacaga   4500
agagtggtat ttgacagtag catcatcttg actgaaacta ttgcaataga ttgggtaggt   4560
cgtaatcttt actggacaga ctatgctctg gaaacaattg aagtctccaa aattgatggg   4620
agccacagga ctgtgctgat tagtaaaaac ctaacaaatc caagaggact agcattagat   4680
cccagaatga atgagcatct actgttctgg tctgactggg gccaccaccc tcgcatcgag   4740
cgagccagca tggacggcag catgcgcact gtcattgtcc aggacaagat cttctggccc   4800
tgcggcttaa ctattgacta ccccaacaga ctgctctact tcatggactc ctatcttgat   4860
tacatggact tttgtgatta taatggacac catcggagac aggtgatagc cagtgatttg   4920
attatacggc acccctatgc cctaactctc tttgaagact ctgtgtactg gactgaccgt   4980
gctactcgtc gggttatgcg agccaacaag tggcatggag ggaaccagtc agttgtaatg   5040
```

```
tataatattc aatggcccct tgggattgtt gcggttcatc cttcgaaaca accaaattcc   5100
gtgaatccat gtgccttttc ccgctgcagc catctctgcc tgctttcctc acaggggcct   5160 cattttact  cctgtgtttg tccttcagga tggagtctgt ctcctgatct cctgaattgc   5220
ttgagagatg atcaacctt  cttaataact gtaaggcaac atataatttt tggaatctcc   5280
cttaatcctg aggtgaagag caatgatgct atggtcccca tagcagggat acagaatggt   5340
ttagatgttg aatttgatga tgctgagcaa tacatctatt gggttgaaaa tccaggtgaa   5400
attcacagag tgaagacaga tggcaccaac aggacagtat ttgcttctat atctatggtg   5460
gggccttcta tgaacctggc cttagattgg atttcaagaa acctttattc taccaatcct   5520
agaactcagt caatcgaggt tttgacactc cacggagata tcagatacag aaaaacattg   5580
attgccaatg atgggacagc tcttggagtt ggctttccaa ttggcataac tgttgatcct   5640
gctcgtggga agctgtactg gtcagaccaa ggaactgaca gtggggttcc tgccaagatc   5700
gccagtgcta acatggatgg cacatctgtg aaaactctct ttactgggaa cctcgaacac   5760
ctggagtgtg tcactcttga catcgaagag cagaaactct actgggcagt cactggaaga   5820
ggagtgattg aaagaggaaa cgtggatgga acagatcgaa tgatcctggt acaccagctt   5880
tcccacccct ggggaattgc agtccatgat tctttccttt attatactga tgaacagtat   5940
gaggtcattg aaagagttga taaggccact ggggccaaca aaatagtctt gagagataat   6000
gttccaaatc tgagggggtct tcaagtttat cacagacgca atgccgccga atcctcaaat   6060
ggctgtagca acaacatgaa tgcctgtcag cagatttgcc tgcctgtacc aggaggattg   6120
ttttcctgcg cctgtgccac tggatttaaa ctcaatcctg ataatcggtc ctgctctcca   6180
tataactctt tcattgttgt ttcaatgctg tctgcaatca gaggcttag  cttggaattg   6240 tcagatcatt cagaaaccat ggtgccggtg gcaggccaag gacgaaacgc actgcatgtg   6300
gatgtggatg tgtcctctgg ctttatttat tggtgtgatt ttagcagctc agtggcatct   6360
gataatgcga tccgtagaat taaaccagat ggatcttctc tgatgaacat tgtgacacat   6420
ggaataggag aaaatggagt ccggggtatt gcagtggatt gggtagcagg aaatctttat   6480
ttcaccaatg cctttgtttc tgaaacactg atagaagttc tgcggatcaa tactacttac   6540
cgccgtgttc ttcttaaagt cacagtggac atgcctaggc atattgttgt agatcccaag   6600
aacagatacc tcttctgggc tgactatggg cagagaccaa agattgagcg ttctttcctt   6660
gactgtacca atcgaacagt gcttgtgtca gagggcattg tcacaccacg gggcttggca   6720
gtggaccgaa gtgatggcta cgtttattgg gttgatgatt ctttagatat aattgcaagg   6780
attcgtatca atggagagaa ctctgaagtg attcgttatg gcagtcgtta cccaactcct   6840
tatggcatca ctgttttga  aaattctatc atatgggtag ataggaattt gaaaaagatc   6900
ttccaagcca gcaaggaacc agagaacaca gagccaccca cagtgataag agacaatatc   6960
aactggctaa gagatgtgac catctttgac aagcaagtcc agcccggtc  accagcagag   7020 gtcaacaaca acccttgctt ggaaaacaat ggtgggtgct ctcatctctg ctttgctctg   7080
cctggattgc acaccccaaa atgtgactgt gcctttggga ccctgcaaag tgatggcaag   7140
aattgtgcca tttcaacaga aaatttcctc atctttgcct tgtctaattc cttgagaagc   7200
ttacacttgg accctgaaaa ccatagccca ccttccaaa  caataaatgt ggaaagaact   7260
gtcatgtctc tagactatga cagtgtaagt gatagaatct acttcacaca aaatttagcc   7320 tctgagttg  gacagatttc ctatgccacc ctgtcttcag ggatccatac tccaactgtc   7380
```

```
attgcttcag gtatagggac tgctgatggc attgcctttg actggattac tagaagaatt    7440
tattacagtg actacctcaa ccagatgatt aattccatgg ctgaagatgg gtctaaccgc    7500
actgtgatag cccgcgttcc aaaaccaaga gcaattgtgt tagatccctg ccaagggtac    7560
ctgtactggg ctgactggga tacacatgcc aaaatcgaga gagccacatt gggaggaaac    7620
ttccgcgtac ccattgtgaa cagcagtctg gtcatgccca gtgggctgac tctggactat    7680
gaagaggacc ttctctactg ggtggatgct agtctgcaga ggattgaacg cagcactctg    7740
acgggcgtgg atcgtgaagt cattgtcaat gcagccgttc atgcttttgg cttgactctc    7800
tatggccagt atatttactg gactgacttg tacacacaaa gaatttaccg agctaacaaa    7860
tatgacgggt caggtcagat tgcaatgacc acaaatttgc tctcccagcc caggggaatc    7920
aacactgttg tgaagaacca gaaacaacag tgtaacaatc cttgtgaaca gtttaatggg    7980
ggctgcagcc atatctgtgc accaggtcca aatggtgccg agtgccagtg tccacatgag    8040
ggcaactggt atttggccaa caacaggaag cactgcattg tggacaatgg tgaacgatgt    8100
ggtgcatctt ccttcacctg ctccaatggg cgctgcatct cggaagagtg gaagtgtgat    8160
aatgacaacg actgtgggga tggcagtgat gagatggaaa gtgtctgtgc acttcacacc    8220
tgctcaccga cagccttcac ctgtgccaat gggcgatgtg tccaatactc ttaccgctgt    8280
gattactaca atgactgtgg tgatggcagt gatgaggcag ggtgcctgtt cagggactgc    8340
aatgccacca cggagtttat tgtgcaataac agaaggtgca tacctcgtga gtttatctgc    8400
aatggtgtag acaactgcca tgataataac acttcagatg agaaaaattg ccctgatcgc    8460
acttgccagt ctggatacac aaaatgtcat aattcaaata tttgtattcc tcgcgtttat    8520
ttgtgtgacg gagacaatga ctgtggagat aacagtgatg aaaaccctac ttattgcacc    8580
actcacacgt gcagcagcag tgagttccaa tgcgcatctg ggcgctgtat tcctcaacat    8640
tggtattgtg atcaagaaac agattgtttt gatgcctctg atgaacctgc ctcttgtggt    8700
cactctgagc gaacatgcct agctgatgag ttcaagtgtg atggtgggag gtgcatccca    8760
agcgaatgga tctgtgacgg tgataatgac tgtgggggata tgagtgacga ggataaaagg    8820
caccagtgtc agaatcaaaa ctgctcggat tccgagtttc tctgtgtaaa tgacagacct    8880
ccggacagga ggtgcattcc ccagtcttgg gtctgtgatg gcgatgtgga ttgtactgac    8940
ggctacgatg agaatcagaa ttgcaccagg agaacttgct ctgaaaatga attcacctgt    9000
ggttacggac tgtgtatccc aaagatattc aggtgtgacc ggcacaatga ctgtggtgac    9060
tatagcgacg agaggggctg cttataccag acttgccaac agaatcagtt tacctgtcag    9120
aacgggcgct gcattagtaa aaccttcgtc tgtgatgagg ataatgactg tggagacgga    9180
tctgatgagc tgatgcacct gtgccacacc ccagaaccca cgtgtccacc tcacgagttc    9240
aagtgtgaca atgggcgctg catcgagatg atgaaactct gcaaccacct agatgactgt    9300
ttggacaaca gcgatgagaa aggctgtggc attaatgaat gccatgaccc ttcaatcagt    9360
ggctgcgatc acaactgcac agacacctta accagtttct attgttcctg tcgtcctggt    9420
tacaagctca tgtctgacaa gcggacttgt gttgatattg atgaatgcac agagatgcct    9480
tttgtctgta gccagaagtg tgagaatgta ataggctcct acatctgtaa gtgtgcccca    9540
ggctacctcc gagaaccaga tggaaagacc tgccggcaaa acagtaacat cgaaccctat    9600 ctcatttta gcaaccgtta ctatttgaga aatttaacta tagatggcta ttttactcc    9660 ctcatccttgg aaggactgga caatgttgtg gcattagatt ttgaccgagt agagaagaga    9720
ttgtattgga ttgatacaca gaggcaagtc attgagagaa tgtttctgaa taagacaaac    9780
```

```
aaggagacaa tcataaacca cagactacca gctgcagaaa gtctggctgt agactgggtt   9840
tccagaaagc tctactggtt ggatgcccgc ctgatggcc tctttgtctc tgacctcaat    9900
ggtggacacc gccgcatgct ggcccagcac tgtgtggatg ccaacaacac cttctgcttt   9960
gataatccca gaggacttgc ccttcaccct caatatgggt acctctactg ggcagactgg  10020
ggtcaccgcg catacattgg gagagtaggc atggatggaa ccaacaagtc tgtgataatc  10080
tccaccaagt tagagtggcc taatggcatc accattgatt acaccaatga tctactctac  10140
tgggcagatg cccacctggg ttacatagag tactctgatt tggagggcca ccatcgacac  10200
acggtgtatg atggggcact gcctcaccct ttcgctatta ccattttgga agacactatt  10260
tattggacag attggaatac aaggacagtg aaaagggaa acaaatatga tggatcaaat    10320
agacagacac tggtgaacac aacacacaga ccatttgaca tccatgtgta ccatccatat  10380
aggcagccca ttgtgagcaa tccctgtggt accaacaatg gtggctgttc tcatctctgc  10440
ctcatcaagc caggaggaaa agggttcact tgcgagtgtc cagatgactt ccgcacccTT  10500
cagctgagtg gcagcaccta ctgcatgccc atgtgctcca gcacccagtt cctgtgcgct  10560
aacaatgaaa agtgcattcc tatctggtgg aaatgtgatg gacagaaaga ctgctcagat  10620
ggctctgatg aactggccct ttgcccgcag cgcttctgcc gactgggaca gttccagtgc  10680
agtgacggca actgcaccag cccgcagact ttatgcaatg ctcaccaaaa ttgccctgat  10740
gggtctgatg aagaccgtct tctttgtgag aatcaccact gtgactccaa tgaatggcag  10800
tgcgccaaca aacgttgcat cccagaatcc tggcagtgtg acacatttaa cgactgtgag  10860
gataactcag atgaagacag ttcccactgt gccagcagga cctgccggcc gggccagttt  10920
cggtgtgcta atggccgctg catcccgcag gcctggaagt gtgatgtgga taatgattgt  10980
ggagaccact cggatgagcc cattgaagaa tgcatgagct ctgcccatct ctgtgacaac  11040
ttcacagaat tcagctgcaa aacaaattac cgctgcatcc caaagtgggc cgtgtgcaat  11100
ggtgtagatg actgcaggga caacagtgat gagcaaggct gtgaggagag gacatgccat  11160
cctgtggggg atttccgctg taaaaatcac cactgcatcc ctcttcgttg gcagtgtgat  11220
gggcaaaatg actgtggaga taactcagat gaggaaaact gtgctccccg ggagtgcaca  11280
gagagcgagt ttcgatgtgt caatcagcag tgcattccct cgcgatggat ctgtgaccat  11340
tacaacgact gtgggacaa ctcagatgaa cgggactgtg agatgaggac ctgccatcct  11400
gaatattttc agtgtacaag tggacattgt gtacacagtg aactgaaatg cgatggatcc  11460
gctgactgtt tggatgcgtc tgatgaagct gattgtccca cacgctttcc tgatggtgca  11520
tactgccagg ctactatgtt cgaatgcaaa aaccatgttt gtatcccgcc atattggaaa  11580
tgtgatggcg atgatgactg tggcgatggt tcagatgaag aacttcacct gtgcttggat  11640
gttccctgta attcaccaaa ccgtttccgg tgtgacaaca atcgctgcat ttatagtcat  11700
gaggtgtgca atggtgtgga tgactgtgga gatggaactg atgagacaga ggagcactgt  11760
agaaaaccga cccctaaacc ttgtacagaa tatgaatata agtgtggcaa tgggcattgc  11820
attccacatg acaatgtgtg tgatgatgcc gatgactgtg gtgactggtc cgatgaactg  11880
ggttgcaata aaggaaaaga aagaacatgt gctgaaaata tatgcgagca aaattgtacc  11940
caattaaatg aaggaggatt tatctgctcc tgtacagctg ggttcgaaac caatgttttt  12000
gacagaacct cctgtctaga tatcaatgaa tgtgaacaat ttgggacttg tcccagcac   12060 tgcagaaata ccaaaggaag ttatgagtgt gtctgtgctg atggcttcac gtctatgagt  12120
```

```
gaccgccctg gaaaacgatg tgcagctgag ggtagctctc ctttgttgct actgcctgac    12180
aatgtccgaa ttcgaaaata taatctctca tctgagaggt tctcagagta tcttcaagat    12240
gaggaatata tccaagctgt tgattatgat tgggatccca aggacatagg cctcagtgtt    12300
gtgtattaca ctgtgcgagg ggagggctct aggtttggtg ctatcaaacg tgcctacatc    12360
cccaactttg aatccggccg caataatctt gtgcaggaag ttgacctgaa actgaaatac    12420
gtaatgcagc cagatggaat agcagtggac tgggttggaa ggcatattta ctggtcagat    12480
gtcaagaata aacgcattga ggtggctaaa cttgatggaa ggtacagaaa gtggctgatt    12540
tccactgacc tggaccaacc agctgctatt gctgtgaatc ccaaactagg gcttatgttc    12600
tggactgact ggggaaagga acctaaaatc gagtctgcct ggatgaatgg agaggaccgc    12660
aacatcctgg ttttcgagga ccttggttgg ccaactggcc tttctatcga ttatttgaac    12720
aatgaccgaa tctactggag tgacttcaag gaggacgtta ttgaaaccat aaaatatgat    12780
gggactgata ggagagtcat tgcaaaggaa gcaatgaacc cttacagcct ggacatcttt    12840
gaagaccagt tatactggat atctaaggaa aagggagaag tatggaaaca aaataaattt    12900
gggcaaggaa agaaagagaa aacgctggta gtgaaccctt ggctcactca agttcgaatc    12960
tttcatcaac tcagatacaa taagtcagtg cccaaccttt gcaaacagat ctgcagccac    13020
ctctgccttc tgagacctgg aggatacagc tgtgcctgtc cccaaggctc cagctttata    13080
gaggggagca ccactgagtg tgatgcagcc atcgaactgc ctatcaacct gccccccca    13140
tgcaggtgca tgcacggagg aaattgctat tttgatgaga ctgacctccc caaatgcaag    13200
tgtcctagcg gctacaccgg aaaatattgt gaaatggcgt tttcaaaagg catctctcca    13260
ggaacaaccg cagtagctgt gctgttgaca atcctcttga tcgtcgtaat tggagctctg    13320
gcaattgcag gattcttcca ctatagaagg accggctccc ttttgcctgc tctgcccaag    13380
ctgccaagct taagcagtct cgtcaagccc tctgaaaatg ggaatggggt gaccttcaga    13440
tcaggggcag atcttaacat ggatattgga gtgtctggtt ttggacctga gactgctatt    13500
gacaggtcaa tggcaatgag tgaagacttt gtcatggaaa tggggaagca gcccataata    13560
tttgaaaacc caatgtactc agccagagac agtgctgtca aagtggttca gccaatccag    13620
gtgactgtat ctgaaaatgt ggataataag aattatggaa gtcccataaa cccttctgag    13680
atagttccag agacaaaccc aacttcacca gctgctgatg gaactcaggt gacaaaatgg    13740
aatctcttca aacgaaaatc taaacaaact accaactttg aaaatccaat ctatgcacag    13800
atggagaacg agcaaaagga aagtgttgct gcgacaccac ctccatcacc ttcgctccct    13860
gctaagccta agcctccttc gagaagagac ccaactccaa cctattctgc aacagaagac    13920
actttaaag acaccgcaaa tcttgttaaa gaagactctg aagtatag                 13968
```

USE OF LRP2 AGONISTS FOR GENERATING MYELOID-DERIVED SUPPRESSOR CELLS

CROSS-REFERENCE TO RELATED APPLICATIONS

This is a National Stage Entry under 35 U.S.C. 371 of International Patent Application No. PCT/US2020/040499, filed Jul. 1, 2020, which claims the benefit under 35 USC 119(e) of U.S. Provisional Patent Application No. 62/869,922, filed Jul. 2, 2019. These applications are incorporated by reference herein.

STATEMENT OF GOVERNMENT LICENSE RIGHTS

This invention was made with government support under grant number P30 CA010815-50 awarded by the National Institutes of Health. The government has certain rights in the invention.

BACKGROUND

Myeloid-derived suppressor cells (MDSCs) are a heterogeneous population of cells that expands during cancer, inflammation and infection, and that has a remarkable ability to suppress T-cell responses. These cells constitute a unique component of the immune system that regulates immune responses in healthy individuals and in the context of various diseases.

MDSCs represent an intrinsic part of the myeloid-cell lineage and are a heterogeneous population that is comprised of myeloid-cell progenitors and precursors of myeloid cells. In healthy individuals, immature myeloid cells (IMCs) generated in bone marrow quickly differentiate into mature granulocytes, macrophages or dendritic cells (DCs). In pathological conditions such as cancer, various infectious diseases, sepsis, trauma, bone marrow transplantation or some autoimmune disorders, a partial block in the differentiation of IMCs into mature myeloid cells results in an expansion of this population. Importantly, the activation of these cells in a pathological context results in the upregulated expression of immune suppressive factors such as arginase (encoded by ARG1) and inducible nitric oxide synthase (iNOS; also known as NOS2) and an increase in the production of NO (nitric oxide) and reactive oxygen species (ROS). Together, this results in the expansion of an IMC population that has immune suppressive activity; these cells are now collectively known as MDSCs.

Inflammation is one of the most complicated processes in the human body, and the promoting and inhibiting mechanisms controlling them are significant players in the pathogenesis of various diseases. MDSCs have been implicated in the pathogenesis of various inflammatory conditions including asthma (Shi et al, Myeloid-derived suppressor cell function is diminished in aspirin-triggered allergic airway hyperresponsiveness in mice, J Allergy Clin Immunol November 2014; 134:1163-74); non-neoplastic inflamed organs (Sendo et al, Myeloid-derived suppressor cells in nonneoplastic inflamed organs. Inflammation and Regeneration (2018) 38:19); and hepatic inflammation and fibrosis (Hammerich and Tacke, Emerging roles of myeloid derived suppressor cells in hepatic inflammation and fibrosis, World J Gastrointest Pathophysiol. 2015 Aug. 15; 6(3):43-50). Although initial observations and most of the current information regarding the role of MDSCs in immune responses has come from studies in the cancer field, accumulating evidence has shown that MDSCs also regulate immune responses in bacterial and parasitic infections, acute and chronic inflammation, traumatic stress, surgical sepsis and transplantation.

What is needed in the art is more effective treatment for inflammatory conditions.

SUMMARY OF THE INVENTION

Provided herein, in one aspect is a method of generating MDSCs ex vivo. The method includes upregulating or expressing LRP2 on blood cells and culturing the blood cells with lactoferrin. In one embodiment, the blood cells are selected from peripheral blood mononuclear cells, cord blood, and bone marrow cells. In another embodiment, the blood cells are CD34+ cells.

In another aspect, a pharmaceutical composition comprising the MSDCs produced by the methods described herein is provided.

In yet another aspect, a method of treating an inflammatory disease in a subject in need thereof is provided. In another aspect, a method of preventing, reducing the likelihood of occurrence or severity of an inflammatory disease in a subject in need thereof is provided. These methods include administering a pharmaceutical composition which includes MDSCs as described herein. In one embodiment, included herein is a method of treating necrotising enterocolitis (NEC).

Other aspects and advantages of the invention will be readily apparent from the following detailed description of the invention.

DETAILED DESCRIPTION OF THE INVENTION

Figure 1:
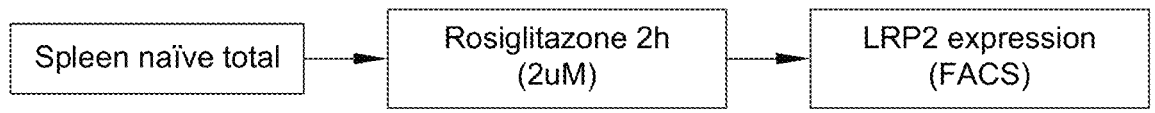
FIG. 1 shows LRP2 expression on Ly6G+-neutrophils (right) and Ly6C+-monocytes (left) from spleen measured before and after rosiglitazone (2 uM) treatment for 2 hours. LRP2 expression in treated neutrophils, and to a lesser-extent monocytes, was increased in rosiglitazone treated cells.
Figure 1:
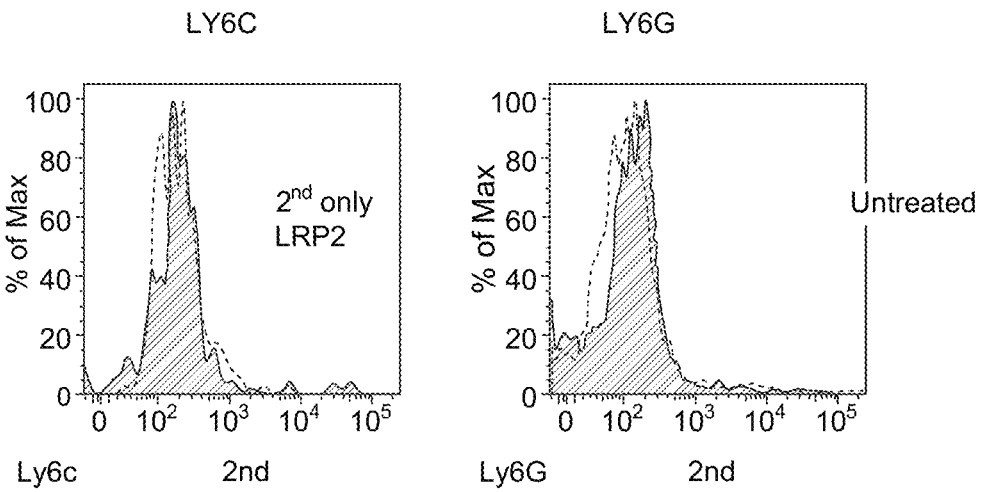
Figure 1:
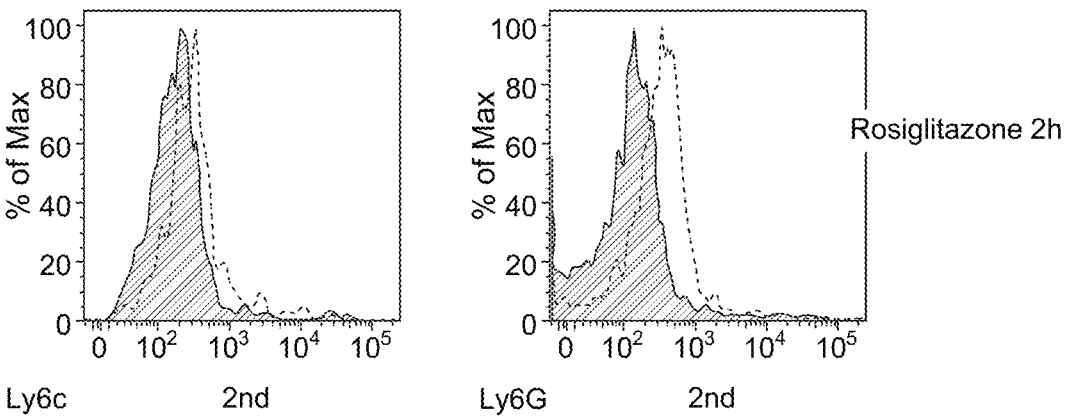

Myeloid-derived suppressor cells (MDSCs) have been implicated in the pathogenesis of inflammatory disease and the inventors have demonstrated that administration of MDSCs are useful in treating certain inflammatory conditions. As described herein, the inventors have shown that culturing certain blood cells with lactoferrin results in generation and expansion of MDSCs.

It is to be noted that the term "a" or "an" refers to one or more. As such, the terms "a" (or "an"), "one or more," and "at least one" are used interchangeably herein.

While various embodiments in the specification are presented using "comprising" language, under other circumstances, a related embodiment is also intended to be interpreted and described using "consisting of" or "consisting essentially of" language. The words "comprise", "comprises", and "comprising" are to be interpreted inclusively rather than exclusively. The words "consist", "consisting", and its variants, are to be interpreted exclusively, rather than inclusively.

As used herein, the term "about" means a variability of 10% from the reference given, unless otherwise specified.

"Upregulate" and "upregulation", as used herein, refer to an elevation in the level of expression of a product of one or more genes in a cell or the cells of a tissue or organ.

A "subject" is a mammal, e.g., a human, mouse, rat, guinea pig, dog, cat, horse, cow, pig, or non-human primate, such as a monkey, chimpanzee, baboon or gorilla. In one embodiment, the subject is a human. The subject may be of any age, as determined by the health care provider. In one embodiment, the subject is a child, i.e., under the age of 18 years old. In another embodiment, the subject is a young child, i.e., 8 years old or less. In another embodiment, the subject is a toddler, i.e., 3 years old or less. In yet another embodiment, the subject is an infant, i.e., 1 year of age or less. In yet another embodiment, the subject is a newborn or neonate, i.e., one month of age or less. In another embodiment, the subject is a preterm infant. In another embodiment, the subject is an adult. In yet another embodiment, the subject is an older adult, i.e., over the age of 35, 40, 45, 50, 55, 60, 65, 70, 75, 80, 85 or 90 years of age.

Lactoferrin (LF) is an iron-binding protein that is secreted by serous epithelial cells and neutrophils that competes with bacteria for iron, thereby inhibiting bacterial growth. LF is expressed in most biological fluids with particularly high levels in mammalian milk. LF can bind and sequester lipopolysaccharides (LPS), thus preventing pro-inflammatory pathway activation, sepsis and tissue damages. LF is also considered a cell-secreted mediator that bridges the innate and adaptive immune responses. See, WO 2017/044979, which is incorporated herein by reference. Lactoferrin is a single-chain iron-binding glycoprotein of approximately 80 kDa that belongs to the human family of transferrins. LF is present in myriad mucosal fluids, but is most predominant in human milk, particularly in the colostrum during early lactation, where it has been suggested to promote the healthy growth and development of the GI tract (Zhang, et al, 2001, Adv. Exp. Med. Biol. 501:107-13), promote the growth of commensal bacterial populations and protect against the establishment of pathogenic bacteria and viruses (Barboza., et al, 2012, Mol. Cell. Proteomics 11:M111 015248; Ochoa, T. J. and Cleary, T. G., 2009, Biochimie 91:30-4; Ammendolia, et al, 2012, Pathog. Glob. Health 106: 12-9). Human colostrums and mature breast milk contain 5.8 mg/mL and 3.3 mg/mL of LF, respectively (Montagne, et al, 1999, J. Pediatr. Gastroenterol. Nutr, 29:75-80; Montagne, et al, 2001, Adv. Exp. Med. Biol. 501:241-7). in contrast, bovine colostrum and milk contain markedly reduced concentrations of LF (1.5 mg/mL in colostral whey and 20-200 ug/mL in milk) (Steijns, et al, 2000, Br. J. Nuts., 84 Suppl. LS11-7). LE has been previously identified for its multifactorial and beneficial activities in several models of human health including inflammation (Mueller, et al, 2011, Curr. Med. Res. Opin. 27:793-7; Zavaleta, et al, 2007, J. Pediatr. Gastroenterol. Nutr. 44:258-64), wound healing (Lyons, et al, 2007, Am. J. Surg, 193:49-54), infectious diseases (Zavaleta, et al, 2007, J. Pediatr. Gastroenterol. Nutr, 44:258-64; King, et al, 2007, J. Pediatr. Gastroenterol. Nutr. 44:245-51; Ochoa, et al, 2008, Clin. Infect. Dis. 46: 1881-3) and cancer (Parikh, et al, 2011, J. Clin. Oncol. 29:4129-36; Hayes, et al, 2010, Invest. New Drugs 28: 156-62). LF has been described for modulation of T cell phenotype in subjects having neurodegenerative or autoimmune disease (WO 2017/044979, which is incorporated herein by reference).

As used herein, the term "lactoferrin" refers to any native lactoferrin and any analog, modification, derivative or fragment thereof. The source of the lactoferrin may be human, or another mammal such as non-human primate, bovine, ovine, porcine, caprine, or murine. In one embodiment, the lactoferrin is a human lactoferrin. Lactoferrin includes the following compounds found in Table 1. Each of these publications is incorporated herein by reference.

TABLE 1

| Lactoferrin compounds | | |
| --- | --- | --- |
| Patent, Application, or Publication Number | Drug name(s) | Description from claims or specification |
| US6066469A | human lactoferrin, recombinant human lactoferrin | human lactoferrin, recombinant human lactoferrin |
| US6455687B1 | human lactoferrin clone, recombinant human lactoferrin clone | human lactoferrin clone, recombinant human lactoferrin clone |
| US7420033 | lactoferrin peptide (33-mer) | A pharmaceutical composition comprising a lactoferrin related peptide (33-mer peptides) |
| US7183381 | talactoferin alfa | A pharmaceutical composition comprising a lactoferrin related peptide; an isolated polypeptide having an amino acid sequence as defined in SEQ ID NO: 10 (lactoferrin related peptide sequence) |

TABLE 1-continued

Lactoferrin compounds

| Patent, Application, or Publication Number | Drug name(s) | Description from claims or specification |
|---|---|---|
| US6111081A | lactoferrin variants | Lactoferrin variants, nucleic acid sequences encoding a lactoferrin variant |
| US6569831B1 | VEN-100, VEN-120, VEN-150 | A recombinant nucleic acid molecule encoding a mature lactoferrin or a lactoferrin-derived protein; a recombinant vector comprising a recombinant nucleic acid molecule encoding a mature lactoferrin or a lactoferrin-derived protein |
| US7354902 | | A mature lactoferrin obtained by a method of producing lactoferrin |
| WO2002064750A2 | | heterologous lactoferrin polypeptide produced in a grain of a plant; codon optimized nucleic acid molecule for expression of polypeptides in monocot, wherein the nucleic acid is a human lactoferrin nucleic acid encoding human lactoferrin |
| WO2017044979A2 | recombinant human lactoferrin (rhLF) | Pharmaceutical composition comprising plant-derived recombinant human lactoferrin |
| EP2668205B1 | PXL-01 | Peptides comprising mature human lactoferrin amino acid sequences |
| US7253143B1 | | purified lactoferrin peptides |
| US20110053833A1 | | Synthetic peptides which can be used for same purposes as lactoferrin, lactoferricin or other lactoferrin derived peptides |
| US8815812B2 | | Isolated peptides and synthetic peptides which can be used for the same purposes as in US20110053833A1 (above) |
| US8673839 | polyethylene glycol-lactoferrin (PEG-lactoferrin) | A biologically active complex of lactoferrin |
| JP5427170 | | Biologically active complex of lactoferrin and PEG |
| EP2030980A1 | hLF-111 (also known as hLF 1-11, hLF 111, hLF1-11, hLF111, Human Lactoferrin Peptide 1-11, Human Lactoferrin | mutants of lactoferrin (polypeptides) |
| 15/847,719 US20180127486A1 | PRC-14, PRC14 | recombinant polypeptide comprising lactoferrin (clinical trial by pharmareview corp preclinical dev for treatment of intracerebral hemmorage) |
| CN105664174A | Lf-HA-DOX | Lf-HA-DOX macromolecule prodrug compound |
| US20140357550A1 | AdeLact | pharmaceutical composition with sustained and rapidly commencing antitoxic effect, based on nanostructures, producing human lactoferrin directly in the body |
| WO2008003688A1 | ALX-009 (Meveol-brand name) | combination of hypothiocyanite (OSCN-) and lactoferrin (used in clinical trial through inhalation for treatment of CF) |

Low-density lipoprotein receptor-related protein 2 (LRP2) is a multiligand endocytic receptor Nvhich acts together with CUBN to mediate endocytosis of high-density lipoproteins. LRP2 is also known as LDL Receptor Related Protein 2, Lipoprotein receptor-related protein-2, Megalin and gp330. LRP2 is found in the plasma membrane of epithelial cells and is a component and auxiliary hedgehog signaling receptor. LRP2 is a multiligand binding receptor: a cell surface receptor for albumin, a receptor for thyroglobulin, amongst others. As shown herein, LRP2 is believed to be the receptor for lactoferrin. The sequence of human LRP2 is known and can be found at UniProtKB-P98164.

```
hLRP2
>sp|P98164|LRP2_HUMAN Low-density lipoprotein
receptor-related
protein 2 OS = Homo sapiens OX = 9606 GN = LRP2
PE = 1 SV = 3
                                          SEQ ID NO: 1
MDRGPAAVACTLLLALVACLAPASGQECDSAHFRCGSGHCIPADWRCDG

TKDCSDDADEIGCAVVTCQQGYFKCQSEGQCIPNSWVCDQDQDCDDGSD

ERQDCSQSTCSSHQITCSNGQCIPSEYRCDHVRDCPDGADENDCQYPTC

EQLTCDNGACYNTSQKCDWKVDCRDSSDEINCTEICLHNEFSCGNGECI
```

-continued

PRAYVCDHDNDCQDGSDEHACNYPTCGGYQFTCPSGRCIYQNWVCDGED
DCKDNGDEDGCESGPHDVHKCSPREWSCPESGRCISIYKVCDGILDCPG
REDENNTSTGKYCSMTLCSALNCQYQCHETPYGGACFCPPGYIINHNDS
RTCVEFDDCQIWGICDQKCESRPGRHLCHCEEGYILERGQYCKANDSFG
EASIIFSNGRDLLIGDIHGRSFRILVESQNRGVAVGVAFHYHLQRVFWT
DTVQNKVFSVDINGLNIQEVLNVSVETPENLAVDWVNNKIYLVETKVNR
IDMVNLDGSYRVTLITENLGHPRGIAVDPTVGYLFFSDWESLSGEPKLE
RAFMDGSNRKDLVKTKLGWPAGVTLDMISKRVYWVDSRFDYIETVTYDG
IQRKTVVHGGSLIPHPFGVSLFEGQVFFTDWTKMAVLKANKFTETNPQV
YYQASLRPYGTVYHSLRQPYATKPCKDNNGGCEQVCVLSHRTDNDGLGF
RCKCTFGFQLDTDERHCIAVQNFLIFSSQVAIRGIPFTLSTQEDVMVPV
SGNPSFFVGIDFDAQDSTIFFSDMSKHMIFKQKIDGTGREILAANRVEN
VESLAFDWISKNLYWTDSHYKSISVMRLADKTRRTVVQYLNNPRSVVVH
PFAGYLFFTDWFRPAKIMRAWSDGSHLLPVINTTLGWPNGLAIDWAASR
LYWVDAYFDKIEHSTFDGLDRRRLGHIEQMTHPFGLAIFGEHLFFTDWR
LGAIIRVRKADGGEMTVIRSGIAYILHLKSYDVNIQTGSNACNQPTHPN
GDCSHFCFPVPNFQRVCGCPYGMRLASNHLTCEGDPTNEPPTEQCGLFS
FPCKNGRCVPNYYLCDGVDDCHDNSDEQLCGTLNNTCSSSAFTCGHGEC
IPAHWRCDKRNDCVDGSDEHNCPTHAPASCLDTQYTCDNHQCISKNWVC
DTDNDCGDGSDEKNCNSTETCQPSQFNCPNHRCIDLSFVCDGDKDCVDG
SDEVGCVLNCTASQFKCASGDKCIGVTNRCDGVFDCSDNSDEAGCPTRP
PGMCHSDEFQCQEDGICIPNFWECDGHPDCLYGSDEHNACVPKTCPSSY
FHCDNGNCIHRAWLCDRDNDCGDMSDEKDCPTQPFRCPSWQWQCLGHNI
CVNLSVVCDGIFDCPNGTDESPLCNGNSCSDFNGGCTHECVQEPFGAKC
LCPLGFLLANDSKTCEDIDECDILGSCSQHCYNMRGSFRCSCDTGYMLE
SDGRTCKVTASESLLLLVASQNKIIADSVTSQVHNIYSLVENGSYIVAV
DFDSISGRIFWSDATQGKTWSAFQNGTDRRVVFDSSIILTETIAIDWVG
RNLYWTDYALETIEVSKIDSHRTVLISKNLTNPRGLALDPRMHEHLLFW
SDGHHPRIERASMDGSMRTVIVQDKIFWPCGLTIDYPNRLLYFMDSYLD
YMDFCDYNGHHRRQVIASDLIIRHPYALTLFEDSVYWTDRATRRVMRAN
KWHGGNQSVVMYNIQWPLGIVAVHPSKQPNSVNPCAFSRCSHLCLLSSQ
GPHFYSCVCPSGWSLSPDLLNCLRDDQPFLITVRQHIIFGISLNPEVKS
NDAMVPIAGIQNGLDVEFDDAEQYIYWVENPGEIHRVKTDGTNRTVFAS
ISMVGPSMNLALDWISRNLYSTNPRTQSIEVLTLHGDIRYRKTLIANDG
TALGVGFPIGITVDPARGKLYWSDQGTDSGVPAKIASANMDGTSVKTLF
TGNLEHLECVTLDIEEQKLYWAVTGRGVIERGNVDGTDRMILVHQLSHP
WGIAVHDSFLYYTDEQYEVIERVDKATGANKIVLRDNVPNLRGLQVYHR
RNAAESSNGCSNNMNACQQICLPVPGGLFSCACATGFKLNPDNRSCSPY
NSFIVVSMLSAIRGFSLELSDHSETMVPVAGQGRNALHVDVDVSSGFIY
WCDFSSSVASDNAIRRIKPDGSSLMNIVTHGIGENGVRGIAVDWVAGNL
YFTNAFVSETLIEVLRINTTYRRVLLKVTVDMPRHIVVDPKNRYLFWAD

-continued

YGQRPKIERSFLDCTNRTVLVSEGIVTPRGLAVDRSDGYVWVDDSLDII
ARIRINGENSEVIRYGSRYPTPYGITVFENSIIWVDRNLKKIFQASKEP
ENTEPPTVIRDNINWLRDVTIFDKQVQPRSPAEVNNNPCLENNGGCSHL
CFALPGLHTPKCDCAFGTLQSDGKNCAISTENFLIFALSNSLRSLHLDP
ENHSPPFQTINVERTVMSLDYDSVSDRIYFTQNLASGVGQISYATLSSG
IHTPTVIASGIGTADGIAFDWITRRIYYSDYLNQMINSMAEDGSNRTVI
ARVPKPRAIVLDPCQGYLYWADWDTHAKIERATLGGNFRVPIVNSSLVM
PSGLTLDYEEDLLWVDASLQRIERSTLTGVDREVIVNAAVHAFGLTLYG
QYIYWTDLYTQRIYRANKYDGSGQIAMTTNLLSQPRGINTVVKNQKQQC
NNPCEQFNGGCSHICAPGPNGAECQCPHEGNWYLANNRKCIVDNGERCG
ASSFTCSNGRCISEEWKCDNDNDCGDGSDEMESVCALHTCSPTAFTCAN
GRCVQYSYRCDYYNDCGDGSDEAGCLFRDCNATTEFMCNNRRCIPREFI
CNGVDNCHDNNTSDEKNCPDRTCQSGYTKCHNSNICIPRVYLCDGDNDC
GDNSDENPTYCTTHTCSSSEFQCASGRCIPQHWYCDQETDCFDASDEPA
SCGHSERTCLADEFKCDGGRCIPSEWICDGDNDCGDMSDEDKRHQCQNQ
NCSDSEFLCVNDRPPDRRCIPQSWVCDGDVDCTDGYDENQNCTRRTCSE
NEFTCGYGLCIPKIFRCDRHNDCGDYSDERGCLYQTCQQNQFTCQNGRC
ISKTFVCDEDNDCGDGSDELMHLCHTPEPTCPPHEFKCDNGRCIEMMKL
CNHLDDCLDNSDEKGCGINECHDPSISGCDHNCTDTLTSFYCSCRPGYK
LMSDKRTCVDIDECTEMPFVCSQKCENVIGSYICKCAPGYLREPDGKTC
RQNSNIEPYLIFSNRYYLRNLTIDGYFYSLILEGLDNVVALDFDRVEKR
LYWIDTQRQVIERMFLNKTNKETIINHRLPAAESLAVDWVSRKLYWLDA
RLDGLFVSDLNGGHRRMLAQHCVDANNTFCFDNPRGLALHPQYGYLYWA
DWGHRAYIGRVGMDGTNKSVIISTKLEWPNGITIDYTNDLLYWASAHLG
YIEYSDLEGHHRHTVYDGALPHPFAITIFEDTIYWTDWNTRTVEKGNKY
DGSNRQTLVNTTHRPFDIHVYHPYRQPIVSNPCGTNNGGCSHLCLIKPG
GKGFTCEPCPDDFRTLQLSGSTYCMPMCSSTQFLCANNEKCIPIWWKCD
GQKDCSDGSDELALCPQRFCRLGQFQCSDGNCTSPQTLCNAHQNCPDGS
DEDRLLCENHHCDSNEWQCANKRCIPESWQCDTFNDCEDNSDEDSSHCA
SRTCRPGQFRCANGRCIPQAWKCDVDNDCGDHSDEPIEECMSSAHLCDN
FTEFSCKTNYRCIPKWAVCNGVDDCRDNSDEQGCEERTCHPVGDFRCKN
HHCIPLRWQCDGQNDCGDNSDEENCAPRECTESEFRCVNQQCIPSRWIC
DHYNDCGDNSDERDCEMRTCHPEYFQCTSGHCVHSELKCDGSADCLDAS
DEADCPTRFPDGAYCQATMFECKNHVCIPPYWKCDGDDDCGDGSDEELH
LCLDVPCNSPNRFRCDNNRCIYSHEVCNGVDDCGDGTDETEEHCRKPTP
KPCTEYEYKCGNGHCIPHDNVCDDADDCGDWSDELGCNKGKERTCAENI
CEQNCTQLNEGGFICSCTAGFETNVFDRTSCLDINECEQFGTCPQHCRN
TKGSYECVCADGFTSMSDRPGKRCAAEGSSPLLLLPDNVRIRKYNLSSE
RFSEYLQDEEYIQAVDYDWDPKDIGLSVVYYTVRGEGSRFGAIKRAYIP
NFESGRNNLVQEVDLKLKYVMQPDGIAVDWVGRHIYWSDVKNKRIEVAK

LDGRYRKWLISTDLDQPAAIAVNPKLGLMFWTDWGKEPKIESAWMNGED

RNILVFEDLGWPTGLSIDYLNNDRIYWSDFKEDVIETIKYDGTDRRVIA

KEAMNPYSLDIFEDQLYWISKEKGEVWKQNKFGQGKKEKTLVVNPWLTQ

VRIFHQLRYNKSVPNLCKQICSHLCLLRPGGYSCACPQGSSFIEGSTTE

CDAAIELPINLPPPCRCMHGGNCYFDETDLPKCKCPSGYTFKYCEMAFS

KGISPGTTAVAVLLTILLIVVIGALAIAGFFHYRRTGSLLPALPKLPSL

SSLVKPSENGNGVTFRSGADLNMDIGVSGFGPETAIDRSMAMSEDFVME

MGKQPIIFENPMYSARDSAVKVVQPIQVTVSENVDNKNYGSPINPSEIV

PETNPTSPAADGTQVTKWNLFKRKSKQTTNFENPIYAQMENEQKESVAA

TPPPSPSLPAKPKPPSRRDPTPTYSATEDTFKDTANLVKEDSEV

The consensus coding sequence for hLRP2 can be found, eg., at NCBI CCDS2232.1.

hLRP2

SEQ ID NO: 2

ATGGATCGCGGGCCGGCAGCAGTGGCGTGCACGCTGCTCCTGGCTCTCGTCGCCTGCCTAGCGCCGGCCA

GTGGCCAAGAATGTGACAGTGCGCATTTTCGCTGTGGAAGTGGGCATTGCATCCCTGCAGACTGGAGGTG

TGATGGGACCAAAGACTGTTCAGATGACGCGGATGAAATTGGCTGCGCTGTTGTGACCTGCCAGCAGGGC

TATTTCAAGTGCCAGAGTGAGGGACAATGCATCCCCAACTCCTGGGTGTGTGACCAAGATCAAGACTGTG

ATGATGGCTCAGATGAACGTCAAGATTGCTCACAAAGTACATGCTCAAGTCATCAGATAACATGCTCCAA

TGGTCAGTGTATCCCAAGTGAATACAGGTGCGACCACGTCAGAGACTGCCCCGATGGAGCTGATGAGAAT

GACTGCCAGTACCCAACATGTGAGCAGCTTACTTGTGACAATGGGGCCTGCTATAACACCAGTCAGAAGT

GTGATTGGAAAGTTGATTGCAGGGACTCCTCAGATGAAATCAACTGCACTGAGATATGCTTGCACAATGA

GTTTTCATGTGGCAATGGAGAGTGTATCCCTCGTGCTTATGTCTGTGACCATGACAATGATTGCCAAGAC

GGCAGTGACGAACATGCTTGCAACTATCCGACCTGCGGTGGTTACCAGTTCACTTGCCCCAGTGGCCGAT

GCATTTATCAAAACTGGGTTTGTGATGGAGAAGATGACTGTAAAGATAATGGAGATGAAGATGGATGTGA

AAGCGGTCCTCATGATGTTCATAAATGTTCCCCAAGAGAATGGTCTTGCCCAGAGTCGGGACGATGCATC

TCCATTTATAAAGTTTGTGATGGGATTTTAGATTGCCCAGGAAGAGAAGATGAAAACAACACTAGTACCG

GAAAATACTGTAGTATGACTCTGTGCTCTGCCTTGAACTGCCAGTACCAGTGCCATGAGACGCCGTATGG

AGGAGCGTGTTTTTGTCCCCCAGGTTATATCATCAACCACAATGACAGCCGTACCTGTGTTGAGTTTGAT

GATTGCCAGATATGGGGAATTTGTGACCAGAAGTGTGAAAGCCGACCTGGCCGTCACCTGTGCCACTGTG

AAGAAGGGTATATCTTGGAGCGTGGACAGTATTGCAAAGCTAATGATTCCTTTGGCGAGGCCTCCATTAT

CTTCTCCAATGGTCGGGATTTGTTAATTGGTGATATTCATGGAAGGAGCTTCCGGATCCTAGTGGAGTCT

CAGAATCGTGGAGTGGCCGTGGGTGTGGCTTTCCACTATCACCTGCAAAGAGTTTTTTGGACAGACACCG

TGCAAAATAAGGTTTTTTCAGTTGACATTAATGGTTTAAATATCCAAGAGGTTCTCAATGTTTCTGTTGA

AACCCCAGAGAACCTGGCTGTGGACTGGGTTAATAATAAAATCTATCTAGTGGAAACCAAGGTCAACCGC

ATAGATATGGTAAATTTGGATGGAAGCTATCGGGTTACCCTTATAACTGAAAACTTGGGGCATCCTAGAG

GAATTGCCGTGGACCCAACTGTTGGTTATTTATTTTCTCAGATTGGGAGAGCCTTTCTGGGGAACCTAA

GCTGGAAAGGGCATTCATGGATGGCAGCAACCGTAAAGACTTGGTGAAAACAAAGCTGGGATGGCCTGCT

GGGGTAACTCTGGATATGATATCGAAGCGTGTTTACTGGGTTGACTCTCGGTTTGATTACATTGAAACTG

TAACTTATGATGGAATTCAAAGGAAGACTGTAGTTCATGGAGGCTCCCTCATTCCTCATCCCTTTGGAGT

AAGCTTATTTGAAGGTCAGGTGTTCTTTACAGATTGGACAAAGATGGCCGTGCTGAAGGCAAACAAGTTC

ACAGAGACCAACCCACAAGTGTACTACCAGGCTTCCTGAGGCCCTATGGAGTGACTGTTTACCATTCCC

TCAGACAGCCCTATGCTACCAATCCGTGTAAAGATAACAATGGGGGCTGTGAGCAGGTCTGTGTCCTCAG

CCACAGAACAGATAATGATGGTTTGGGTTTCCGTTGCAAGTGCACATTCGGCTTCCAACTGGATACAGAT

GAGCGCCACTGCATTGCTGTTCAGAATTTCCTCATTTTTTCATCCCAAGTTGCTATTCGTGGGATCCCGT

TCACCTTGTCTACCCAGGAAGATGTCATGGTTCCAGTTTCGGGGAATCCTTCTTTCTTTGTCGGGATTGA

-continued

```
TTTTGACGCCCAGGACAGCACTATCTTTTTTTCAGATATGTCAAAACACATGATTTTTAAGCAAAAGATT
GATGGCACAGGAAGAGAAATTCTCGCAGCTAACAGGGTGGAAATGTTGAAAGTTTGGCTTTTGATTGGA
TTTCAAAGAATCTCTATTGGACAGACTCTCATTACAAGAGTATCAGTGTCATGAGGCTAGCTGATAAAAC
GAGACGCACAGTAGTTCAGTATTTAAATAACCCACGGTCGGTGGTAGTTCATCCTTTTGCCGGGTATCTA
TTCTTCACTGATTGGTTCCGTCCTGCTAAAATTATGAGAGCATGGAGTGACGGATCTCACCTCTTGCCTG
TAATAAACACTACTCTTGGATGGCCCAATGGCTTGGCCATCGATTGGGCTGCTTCACGATTGTACTGGGT
AGATGCCTATTTTGATAAAATTGAGCACAGCACCTTTGATGGTTTAGACAGAAGAAGACTGGGCCATATA
GAGCAGATGACACATCCGTTTGGACTTGCCATCTTTGGAGAGCATTTATTTTTTACTGACTGGAGACTGG
GTGCCATTATTCGAGTCAGGAAAGCAGATGGTGGAGAAATGACAGTTATCCGAAGTGGCATTGCTTACAT
ACTGCATTTGAAATCGTATGATGTCAACATCCAGACTGGTTCTAACGCCTGTAATCAACCCACGCATCCT
AACGGTGACTGCAGCCACTTCTGCTTCCCGGTGCCAAATTTCCAGCGAGTGTGTGGGTGCCCTTATGGAA
TGAGGCTGGCTTCCAATCACTTGACATGCGAGGGGGACCCAACCAATGAACCACCCACAGAGCAGTGTGG
CTTATTTTCCTTCCCCTGTAAAAATGGCAGATGTGTGCCCAATTACTATCTCTGTGATGGAGTCGATGAT
TGTCATGATAACAGTGATGAGCAACTATGTGGCACACTTAATAATACCTGTTCATCTTCGGCGTTCACCT
GTGGCCATGGGGAGTGCATTCCTGCACACTGGCGCTGTGACAAACGCAACGACTGTGTGGATGGCAGTGA
TGAGCACAACTGCCCCACCCACGCACCTGCTTCCTGCCTTGACACCCAATACACCTGTGATAATCACCAG
TGTATCTCAAAGAACTGGGTCTGTGACACAGACAATGATTGTGGGGATGGATCTGATGAAAAGAACTGCA
ATTCGACAGAGACATGCCAACCTAGTCAGTTTAATTGCCCCAATCATCGATGTATTGACCTATCGTTTGT
CTGTGATGGTGACAAGGATTGTGTTGATGGATCTGATGAGGTTGGTTGTGTATTAAACTGTACTGCTTCT
CAATTCAAGTGTGCCAGTGGGGATAAATGTATTGGCGTCACAAATCGTTGTGATGGTGTTTTTGATTGCA
GTGACAACTCGGATGAAGCAGGCTGTCCAACCAGGCCTCCTGGTATGTGCCACTCAGATGAATTTCAGTG
CCAAGAAGATGGTATCTGCATCCCGAACTTCTGGGAATGTGATGGGCATCCAGACTGCCTCTATGGATCT
GATGAGCACAATGCCTGTGTCCCCAAGACTTGCCCTTCATCATATTTCCACTGTGACAACGGAAACTGCA
TCCACAGGGCATGGCTCTGTGATCGGGACAATGACTGCGGGGATATGAGTGATGAGAAGGACTGCCCTAC
TCAGCCCTTTCGCTGTCCTAGTTGGCAATGGCAGTGTCTTGGCCATAACATCTGTGTGAATCTGAGTGTA
GTGTGTGATGGCATCTTTGACTGCCCCAATGGGACAGATGAGTCCCCACTTTGCAATGGGAACAGCTGCT
CAGATTTCAATGGTGGTTGTACTCACGAGTGTGTTCAAGAGCCCTTTGGGGCTAAATGCCTATGTCCATT
GGGATTCTTACTTGCCAATGATTCTAAGACCTGTGAAGACATAGATGAATGTGATATTCTAGGCTCTTGT
AGCCAGCACTGTTACAATATGAGAGGTTCTTTCCGGTGCTCGTGTGATACAGGCTACATGTTAGAAAGTG
ATGGGAGGACTTGCAAAGTTACAGCATCTGAGAGTCTGCTGTTACTTGTGGCAAGTCAGAACAAAATTAT
TGCCGACAGTGTCACCTCCCAGGTCCACAATATCTATTCATTGGTCGAGAATGGTTCTTACATTGTAGCT
GTTGATTTTGATTCAATTAGTGGTCGTATCTTTTGGTCTGATGCAACTCAGGGTAAAACCTGGAGTGCGT
TTCAAAATGGAACGGACAGAAGAGTGGTATTTGACAGTAGCATCATCTTGACTGAAACTATTGCAATAGA
TTGGGTAGGTCGTAATCTTTACTGGACAGACTATGCTCTGGAAACAATTGAAGTCTCCAAAATTGATGGG
AGCCACAGGACTGTGCTGATTAGTAAAAACCTAACAAATCCAAGAGGACTAGCATTAGATCCCAGAATGA
ATGAGCATCTACTGTTCTGGTCTGACTGGGGCCACCACCCTCGCATCGAGCGAGCCAGCATGGACGGCAG
CATGCGCACTGTCATTGTCCAGGACAAGATCTTCTGGCCCTGCGGCTTAACTATTGACTACCCCAACAGA
CTGCTCTACTTCATGGACTCCTATCTTGATTACATGGACTTTTGTGATTATAATGGACACCATCGGAGAC
AGGTGATAGCCAGTGATTTGATTATACGGCACCCCTATGCCCTAACTCTCTTTGAAGACTCTGTGTACTG
GACTGACCGTGCTACTCGTCGGGTTATGCGAGCCAACAAGTGGCATGGAGGGAACCAGTCAGTTGTAATG
TATAATATTCAATGGCCCCTTGGGATTGTTGCGGTTCATCCTTCGAAACAACCAAATTCCGTGAATCCAT
```

```
-continued
GTGCCTTTTCCCGCTGCAGCCATCTCTGCCTGCTTTCCTCACAGGGGCCTCATTTTTACTCCTGTGTTTG

TCCTTCAGGATGGAGTCTGTCTCCTGATCTCCTGAATTGCTTGAGAGATGATCAACCTTTCTTAATAACT

GTAAGGCAACATATAATTTTTGGAATCTCCCTTAATCCTGAGGTGAAGAGCAATGATGCTATGGTCCCCA

TAGCAGGGATACAGAATGGTTTAGATGTTGAATTTGATGATGCTGAGCAATACATCTATTGGGTTGAAAA

TCCAGGTGAAATTCACAGAGTGAAGACAGATGGCACCAACAGGACAGTATTTGCTTCTATATCTATGGTG

GGGCCTTCTATGAACCTGGCCTTAGATTGGATTTCAAGAAACCTTTATTCTACCAATCCTAGAACTCAGT

CAATCGAGGTTTTGACACTCCACGGAGATATCAGATACAGAAAAACATTGATTGCCAATGATGGGACAGC

TCTTGGAGTTGGCTTTCCAATTGGCATAACTGTTGATCCTGCTCGTGGGAAGCTGTACTGGTCAGACCAA

GGAACTGACAGTGGGGTTCCTGCCAAGATCGCCAGTGCTAACATGGATGGCACATCTGTGAAAACTCTCT

TTACTGGGAACCTCGAACACCTGGAGTGTGTCACTCTTGACATCGAAGAGCAGAAACTCTACTGGGCAGT

CACTGGAAGAGGAGTGATTGAAAGAGGAAACGTGGATGGAACAGATCGAATGATCCTGGTACACCAGCTT

TCCCACCCCTGGGGAATTGCAGTCCATGATTCTTTCCTTTATTATACTGATGAACAGTATGAGGTCATTG

AAAGAGTTGATAAGGCCACTGGGGCCAACAAAATAGTCTTGAGAGATAATGTTCCAAATCTGAGGGGTCT

TCAAGTTTATCACAGACGCAATGCCGCCGAATCCTCAAATGGCTGTAGCAACAACATGAATGCCTGTCAG

CAGATTTGCCTGCCTGTACCAGGAGGATTGTTTTCCTGCGCCTGTGCCACTGGATTTAAACTCAATCCTG

ATAATCGGTCCTGCTCTCCATATAACTCTTTCATTGTTGTTTCAATGCTGTCTGCAATCAGAGGCTTTAG

CTTGGAATTGTCAGATCATTCAGAAACCATGGTGCCGGTGGCAGGCCAAGGACGAAACGCACTGCATGTG

GATGTGGATGTGTCCTCTGGCTTTATTTATTGGTGTGATTTTAGCAGCTCAGTGGCATCTGATAATGCGA

TCCGTAGAATTAAACCAGATGGATCTTCTCTGATGAACATTGTGACACATGGAATAGGAGAAAATGGAGT

CCGGGGTATTGCAGTGGATTGGGTAGCAGGAAATCTTTATTTCACCAATGCCTTTGTTTCTGAAACACTG

ATAGAAGTTCTGCGGATCAATACTACTTACCGCCGTGTTCTTCTTAAAGTCACAGTGGACATGCCTAGGC

ATATTGTTGTAGATCCCAAGAACAGATACCTCTTCTGGGCTGACTATGGGCAGAGACCAAAGATTGAGCG

TTCTTTCCTTGACTGTACCAATCGAACAGTGCTTGTGTCAGAGGGCATTGTCACACCACGGGGCTTGGCA

GTGGACCGAAGTGATGGCTACGTTTATTGGGTTGATGATTCTTTAGATATAATTGCAAGGATTCGTATCA

ATGGAGAGAACTCTGAAGTGATTCGTTATGGCAGTCGTTACCCAACTCCTTATGGCATCACTGTTTTTGA

AAATTCTATCATATGGGTAGATAGGAATTTGAAAAAGATCTTCCAAGCCAGCAAGGAACCAGAGAACACA

GAGCCACCCACAGTGATAAGAGACAATATCAACTGGCTAAGAGATGTGACCATCTTTGACAAGCAAGTCC

AGCCCCGGTCACCAGCAGAGGTCAACAACAACCCTTGCTTGGAAAACAATGGTGGGTGCTCTCATCTCTG

CTTTGCTCTGCCTGGATTGCACACCCCAAAATGTGACTGTGCCTTTGGGACCCTGCAAAGTGATGGCAAG

AATTGTGCCATTTCAACAGAAAATTTCCTCATCTTTGCCTTGTCTAATTCCTTGAGAAGCTTACACTTGG

ACCCTGAAACCATAGCCCACCTTTCCAAACAATAAATGTGGAAAGAACTGTCATGTCTCTAGACTATGA

CAGTGTAAGTGATAGAATCTACTTCACACAAAATTTAGCCTCTGGAGTTGGACAGATTTCCTATGCCACC

CTGTCTTCAGGGATCCATACTCCAACTGTCATTGCTTCAGGTATAGGGACTGCTGATGGCATTGCCTTTG

ACTGGATTACTAGAAGAATTTATTACAGTGACTACCTCAACCAGATGATTAATTCCATGGCTGAAGATGG

GTCTAACCGCACTGTGATAGCCCGCGTTCCAAAACCAAGAGCAATTGTGTTAGATCCCTGCCAAGGGTAC

CTGTACTGGGCTGACTGGGATACACATGCCAAAATCGAGAGAGCCACATTGGGAGGAAACTTCCGCGTAC

CCATTGTGAACAGCAGTCTGGTCATGCCCAGTGGGCTGACTCTGGACTATGAAGAGGACCTTTCTCTACTG

GGTGGATGCTAGTCTGCAGAGGATTGAACGCAGCACTCTGACGGGCGTGGATCGTGAAGTCATTGTCAAT

GCAGCCGTTCATGCTTTTGGCTTGACTCTCTATGGCCAGTATATTTACTGGACTGACTTGTACACACAAA

GAATTTACCGAGCTAACAAATATGACGGGTCAGGTCAGATTGCAATGACCACAAATTTGCTCTCCCAGCC
```

-continued

```
CAGGGGAATCAACACTGTTGTGAAGAACCAGAAACAACAGTGTAACAATCCTTGTGAACAGTTTAATGGG

GGCTGCAGCCATATCTGTGCACCAGGTCCAAATGGTGCCGAGTGCCAGTGTCCACATGAGGGCAACTGGT

ATTTGGCCAACAACAGGAAGCACTGCATTGTGGACAATGGTGAACGATGTGGTGCATCTTCCTTCACCTG

CTCCAATGGGCGCTGCATCTCGGAAGAGTGGAAGTGTGATAATGACAACGACTGTGGGGATGGCAGTGAT

GAGATGGAAAGTGTCTGTGCACTTCACACCTGCTCACCGACAGCCTTCACCTGTGCCAATGGGCGATGTG

TCCAATACTCTTACCGCTGTGATTACTACAATGACTGTGGTGATGGCAGTGATGAGGCAGGGTGCCTGTT

CAGGGACTGCAATGCCACCACGGAGTTTATGTGCAATAACAGAAGGTGCATACCTCGTGAGTTTATCTGC

AATGGTGTAGACAACTGCCATGATAATAACACTTCAGATGAGAAAAATTGCCCTGATCGCACTTGCCAGT

CTGGATACACAAAATGTCATAATTCAAATATTTGTATTCCTCGCGTTTATTTGTGTGACGGAGACAATGA

CTGTGGAGATAACAGTGATGAAAACCCTACTTATTGCACCACTCACACGTGCAGCAGCAGTGAGTTCCAA

TGCGCATCTGGGCGCTGTATTCCTCAACATTGGTATTGTGATCAAGAAACAGATTGTTTTGATGCCTCTG

ATGAACCTGCCTCTTGTGGTCACTCTGAGCGAACATGCCTAGCTGATGAGTTCAAGTGTGATGGTGGGAG

GTGCATCCCAAGCGAATGGATCTGTGACGGTGATAATGACTGTGGGGATATGAGTGACGAGGATAAAAGG

CACCAGTGTCAGAATCAAAACTGCTCGGATTCCGAGTTTCTCTGTGTAAATGACAGACCTCCGGACAGGA

GGTGCATTCCCCAGTCTTGGGTCTGTGATGGCGATGTGGATTGTACTGACGGCTACGATGAGAATCAGAA

TTGCACCAGGAGAACTTGCTCTGAAAATGAATTCACCTGTGGTTACGGACTGTGTATCCCAAAGATATTC

AGGTGTGACCGGCACAATGACTGTGGTGACTATAGCGACGAGAGGGGCTGCTTATACCAGACTTGCCAAC

AGAATCAGTTTACCTGTCAGAACGGGCGCTGCATTAGTAAAACCTTCGTCTGTGATGAGGATAATGACTG

TGGAGACGGATCTGATGAGCTGATGCACCTGTGCCACACCCCAGAACCCACGTGTCCACCTCACGAGTTC

AAGTGTGACAATGGGCGCTGCATCGAGATGATGAAACTCTGCAACCACCTAGATGACTGTTTGGACAACA

GCGATGAGAAAGGCTGTGGCATTAATGAATGCCATGACCCTTCAATCAGTGGCTGCGATCACAACTGCAC

AGACACCTTAACCAGTTTCTATTGTTCCTGTCGTCCTGGTTACAAGCTCATGTCTGACAAGCGGACTTGT

GTTGATATTGATGAATGCACAGAGATGCCTTTTGTCTGTAGCCAGAAGTGTGAGAATGTAATAGGCTCCT

ACATCTGTAAGTGTGCCCCAGGCTACCTCCGAGAACCAGATGGAAAGACCTGCCGGCAAAACAGTAACAT

CGAACCCTATCTCATTTTTAGCAACCGTTACTATTTGAGAAATTTAACTATAGATGGCTATTTTTACTCC

CTCATCTTGGAAGGACTGGACAATGTTGTGGCATTAGATTTTGACCGAGTAGAGAAGAGATTGTATTGGA

TTGATACACAGAGGCAAGTCATTGAGAGAATGTTTCTGAATAAGACAAACAAGGAGACAATCATAAACCA

CAGACTACCAGCTGCAGAAAGTCTGGCTGTAGACTGGGTTTCCAGAAAGCTCTACTGGTTGGATGCCCGC

CTGGATGGCCTCTTTGTCTCTGACCTCAATGGTGGACACCGCCGCATGCTGGCCCAGCACTGTGTGGATG

CCAACAACACCTTCTGCTTTGATAATCCCAGAGGACTTGCCCTTCACCCTCAATATGGGTACCTCTACTG

GGCAGACTGGGGTCACCGCGCATACATTGGGAGAGTAGGCATGGATGGAACCAACAAGTCTGTGATAATC

TCCACCAAGTTAGAGTGGCCTAATGGCATCACCATTGATTACACCAATGATCTACTCTACTGGGCAGATG

CCCACCTGGGTTACATAGAGTACTCTGATTTGGAGGGCCACCATCGACACACGGTGTATGATGGGGCACT

GCCTCACCCTTTCGCTATTACCATTTTTGAAGACACTATTTATTGGACAGATTGGAATACAAGGACAGTG

GAAAAGGGAAACAAATATGATGGATCAAATAGACAGACACTGGTGAACACAACACACAGACCATTTGACA

TCCATGTGTACCATCCATATAGGCAGCCCATTGTGAGCAATCCCTGTGGTACCAACAATGGTGGCTGTTC

TCATCTCTGCCTCATCAAGCCAGGAGGAAAAGGGTTCACTTGCGAGTGTCCAGATGACTTCCGCACCCTT

CAGCTGAGTGGCAGCACCTACTGCATGCCCATGTGCTCCAGCACCCAGTTCCTGTGCGCTAACAATGAAA

AGTGCATTCCTATCTGGTGGAAATGTGATGGACAGAAAGACTGCTCAGATGGCTCTGATGAACTGGCCCT

TTGCCCCGCAGCGCTTCTGCCGACTGGGACAGTTCCAGTGCAGTGACGGCAACTGCACCAGCCCGCAGACT

TTATGCAATGCTCACCAAAATTGCCCTGATGGGTCTGATGAAGACCGTCTTCTTTGTGAGAATCACCACT
```

-continued

```
GTGACTCCAATGAATGGCAGTGCGCCAACAAACGTTGCATCCCAGAATCCTGGCAGTGTGACACATTTAA

CGACTGTGAGGATAACTCAGATGAAGACAGTTCCCACTGTGCCAGCAGGACCTGCCGGCCGGGCCAGTTT

CGGTGTGCTAATGGCCGCTGCATCCCGCAGGCCTGGAAGTGTGATGTGGATAATGATTGTGGAGACCACT

CGGATGAGCCCATTGAAGAATGCATGAGCTCTGCCCATCTCTGTGACAACTTCACAGAATTCAGCTGCAA

AACAAATTACCGCTGCATCCCAAAGTGGGCCGTGTGCAATGGTGTAGATGACTGCAGGGACAACAGTGAT

GAGCAAGGCTGTGAGGAGAGGACATGCCATCCTGTGGGGGATTTCCGCTGTAAAAATCACCACTGCATCC

CTCTTCGTTGGCAGTGTGATGGGCAAAATGACTGTGGAGATAACTCAGATGAGGAAAACTGTGCTCCCCG

GGAGTGCACAGAGAGCGAGTTTCGATGTGTCAATCAGCAGTGCATTCCCTCGCGATGGATCTGTGACCAT

TACAACGACTGTGGGGACAACTCAGATGAACGGGACTGTGAGATGAGGACCTGCCATCCTGAATATTTTC

AGTGTACAAGTGGACATTGTGTACACAGTGAACTGAAATGCGATGGATCCGCTGACTGTTTGGATGCGTC

TGATGAAGCTGATTGTCCCACACGCTTTCCTGATGGTGCATACTGCCAGGCTACTATGTTCGAATGCAAA

AACCATGTTTGTATCCCGCCATATTGGAAATGTGATGGCGATGATGACTGTGGCGATGGTTCAGATGAAG

AACTTCACCTGTGCTTGGATGTTCCCTGTAATTCACCAAACCGTTTCCGGTGTGACAACAATCGCTGCAT

TTATAGTCATGAGGTGTGCAATGGTGTGGATGACTGTGGAGATGAACTGATGAGACAGAGGAGCACTGT

AGAAAACCGACCCCTAAACCTTGTACAGAATATGAATATAAGTGTGGCAATGGGCATTGCATTCCACATG

ACAATGTGTGTGATGATGCCGATGACTGTGGTGACTGGTCCGATGAACTGGGTTGCAATAAAGGAAAAGA

AAGAACATGTGCTGAAAATATATGCGAGCAAAATTGTACCCAATTAAATGAAGGAGGATTTATCTGCTCC

TGTACAGCTGGGTTCGAAACCAATGTTTTTGACAGAACCTCCTGTCTAGATATCAATGAATGTGAACAAT

TTGGGACTTGTCCCCAGCACTGCAGAAATACCAAAGGAAGTTATGAGTGTGTCTGTGCTGATGGCTTCAC

GTCTATGAGTGACCGCCCTGGAAAACGATGTGCAGCTGAGGGTAGCTCTCCTTTGTTGCTACTGCCTGAC

AATGTCCGAATTCGAAAATATAATCTCTCATCTGAGAGGTTCTCAGAGTATCTTCAAGATGAGGAATATA

TCCAAGCTGTTGATTATGATTGGGATCCCAAGGACATAGGCCTCAGTGTTGTGTATTACACTGTGCGAGG

GGAGGGCTCTAGGTTTGGTGCTATCAAACGTGCCTACATCCCCAACTTTGAATCCGGCCGCAATAATCTT

GTGCAGGAAGTTGACCTGAAACTGAAATACGTAATGCAGCCAGATGGAATAGCAGTGGACTGGGTTGGAA

GGCATATTTACTGGTCAGATGTCAAGAATAAACGCATTGAGGTGGCTAAACTTGATGGAAGGTACAGAAA

GTGGCTGATTTCCACTGACCTGGACCAACCAGCTGCTATTGCTGTGAATCCCAAACTAGGGCTTATGTTC

TGGACTGACTGGGGAAAGGAACCTAAAATCGAGTCTGCCTGGATGAATGGAGAGGACCGCAACATCCTGG

TTTTCGAGGACCTTGGTTGGCCAACTGGCCTTTCTATCGATTATTTGAACAATGACCGAATCTACTGGAG

TGACTTCAAGGAGGACGTTATTGAAACCATAAAATATGATGGGACTGATAGGAGAGTCATTGCAAAGGAA

GCAATGAACCCTTACAGCCTGGACATCTTTGAAGACCAGTTATACTGGATATCTAAGGAAAAGGGAGAAG

TATGGAAACAAAATAAATTTGGGCAAGGAAAGAAAGAGAAAACGCTGGTAGTGAACCCTTGGCTCACTCA

AGTTCGAATCTTTCATCAACTCAGATACAATAAGTCAGTGCCCAACCTTTGCAAACAGATCTGCAGCCAC

CTCTGCCTTCTGAGACCTGGAGGATACAGCTGTGCCTGTCCCCAAGGCTCCAGCTTTATAGAGGGGAGCA

CCACTGAGTGTGATGCAGCCATCGAACTGCCTATCAACCTGCCCCCCCCATGCAGGTGCATGCACGGAGG

AAATTGCTATTTTGATGAGACTGACCTCCCCAAATGCAAGTGTCCTAGCGGCTACACCGGAAAATATTGT

GAAATGGCGTTTTCAAAAGGCATCTCTCCAGGAACAACCGCAGTAGCTGTGCTGTTGACAATCCTCTTGA

TCGTCGTAATTGGAGCTCTGGCAATTGCAGGATTCTTCCACTATAGAAGGACCGGCTCCCTTTTGCCTGC

TCTGCCCAAGCTGCCAAGCTTAAGCAGTCTCGTCAAGCCCTCTGAAAATGGGAATGGGGTGACCTTCAGA

TCAGGGGCAGATCTTAACATGGATATTGGAGTGTCTGGTTTTGGACCTGAGACTGCTATTGACAGGTCAA

TGGCAATGAGTGAAGACTTTGTCATGGAAATGGGGAAGCAGCCCATAATATTTGAAAACCCAATGTACTC
```

-continued

```
AGCCAGAGACAGTGCTGTCAAAGTGGTTCAGCCAATCCAGGTGACTGTATCTGAAAATGTGGATAATAAG

AATTATGGAAGTCCCATAAACCCTTCTGAGATAGTTCCAGAGACAAACCCAACTTCACCAGCTGCTGATG

GAACTCAGGTGACAAAATGGAATCTCTTCAAACGAAAATCTAAACAAACTACCAACTTTGAAAATCCAAT

CTATGCACAGATGGAGAACGAGCAAAAGGAAAGTGTTGCTGCGACACCACCTCCATCACCTTCGCTCCCT

GCTAAGCCTAAGCCTCCTTCGAGAAGAGACCCAACTCCAACCTATTCTGCAACAGAAGACACTTTTAAAG

ACACCGCAAATCTTGTTAAAGAAGACTCTGAAGTATAG
```

As used herein, the term "LRP2 agonist" is any substance which acts to increase the amount or expression of LRP2.

The terms "analog", "modification" and "derivative" refer to biologically active derivatives of the reference molecule that retain desired activity as described herein in general, the term "analog" refers to compounds having a native polypeptide sequence and structure with one or more amino acid additions, substitutions (generally conservative in nature and/or deletions, relative to the native molecule, so long as the modifications do not destroy activity and which are "substantially homologous" to the reference molecule as defined herein. Preferably, the analog, modification or derivative has at least the same desired activity as the native molecule, although not necessarily at the same level. The terms also encompass purposeful mutations that are made to the reference molecule. Particularly preferred modifications include substitutions that are conservative in nature, i.e., those substitutions that take place within a family of amino acids that are related in their side chains. Specifically, amino acids are generally divided into four families: acidic, basic, non-polar and uncharged polar. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the molecule of interest may include up to about 5-20 conservative or non-conservative amino acid substitutions, so long as the desired function of the molecule remains intact. One of skill in the art can readily determine regions of the molecule of interest that can tolerate change by reference to Hopp/ Woods and Kyte Doolittle plots, well known in the art.

By "fragment" is intended a molecule consisting of only a part of the intact full-length polypeptide sequence and structure. The fragment can include a C terminal deletion, an N terminal deletion, and/or an internal deletion of the native polypeptide. A fragment will generally include at least about 5-10 contiguous amino acid residues of the full length molecule, preferably at least about 15-25 contiguous amino acid residues of the full length molecule, and most preferably at least about 20 50 or more contiguous amino acid residues of the full length molecule, or any integer between 5 amino acids and the full length sequence, provided that the fragment in question retains the ability to elicit the desired biological response, although not necessarily at the same level.

The term "derived from" is used to identify the original source of a molecule (e.g., bovine or human) but is not meant to limit the method by which the molecule is made which can be, for example, by chemical synthesis or recombinant means.

As used herein, the term "a therapeutically effective amount" refers an amount sufficient to achieve the intended purpose. For example, an effective amount of lactoferrin will cause generation and expansion of MDSCs as the term is defined herein. An effective amount of MDSCs will inhibit the immune system, including suppression of T cells. An effective amount for treating or ameliorating a disorder, disease, or medical condition is an amount sufficient to result in a reduction or complete removal of the symptoms of the disorder, disease, or medical condition. The effective amount of a given therapeutic agent will vary with factors such as the nature of the agent, the route of administration, the size and species of the animal to receive the therapeutic agent, and the purpose of the administration. The effective amount in each individual case may be determined by a skilled artisan according to established methods in the art.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodiwn stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences, 18th Ed., Gennaro, ed. (Mack Publishing Co., 1990). The formulation should suit the mode of administration.

Routes of administration include, but are not limited to, intradermal, intramuscular, intraperitoneal, intravenous, subcutaneous, intranasal, epidural, and oral routes. The agent may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

Myeloid-derived suppressor cells (MDSCs) are pathologically activated and relatively immature myeloid cells that have been implicated in the immunological regulation of many pathologic conditions. Phenotypically and morphologically, MDSCs are similar to neutrophils (polymorphonuclear) (PMN-MDSCs) and monocytes (M-MDSCs). However, they have potent suppressive activity and distinct gene expression profiles and biochemical characteristics. No or very few MDSCs are observed in steady state physiological conditions. Therefore, until recently, accumulation of MDSCs was considered a consequence of pathological processes or pregnancy.

As noted above, MDSCs can be grouped into subsets: PMN-MDSC and M-MDSC, which are phenotypically and morphologically distinct, and also have unique (although partially overlapping) functional characteristics and biochemical traits, which reflect their different roles under various pathological conditions. MDSCs can have multiple phenotypes, including PMN-MDSC ($CD11b^+Ly6G^+Ly6C^{lo}$) and M-MDSC ($CD11b^+Ly6G^-Ly6C^{hi}$). As used herein, the term MDSC refers to all cells having the phenotype, morphology and/or activity of a MDSC. Such criteria include those described by Bronte et al, Recommendations for myeloid-derived suppressor cell nomenclature and characterization standards, Nat Commun. 2016; 7: 12150, which is incorporated herein by reference. Such activity includes the suppression of T cells. Methods to evaluate suppressive activity are known in the art and are further described herein. Other indicia of MDSC activity include the ability to control inflammation, decrease presence of leukocytes, decrease amounts of IgE, decrease amounts of IL-13 and/or decrease amounts of IL-14. Methods are known in the art for assaying these properties.

As used herein, "disease", "disorder" and "condition" are used interchangeably, to indicate an abnormal state in a subject, As used herein, the term inflammatory condition or inflammatory disease refers to a disorder in which the immune system attacks the body's own cells or tissues, resulting in abnormal inflammation. Inflammation includes or results in chronic pain, redness, swelling, stiffness, and damage to normal tissues. The term inflammatory condition or disease includes autoimmune diseases such as multiple sclerosis, lupus, asthma, autoimmune hepatitis, diabetes, rheumatoid arthritis, psoriasis, inflammatory bowel disease, Addison's disease, Graves' disease, Sjögren's syndrome, Hashimoto's thyroiditis, myasthenia gravis, vasculitis, pernicious anemia, and celiac disease. Other inflammatory conditions include bacterial infections, colitis, osteoarthritis, and allergy. In one embodiment, the inflammatory condition is asthma. In another embodiment, the inflammatory condition is hepatitis. In yet another embodiment, the inflammatory condition is colitis. In one embodiment, the inflammatory condition is necrotising enterocolitis (NEC).

Methods of Generating MSC

In one aspect, provided herein are methods of generating MDSCs ex vivo. The method includes upregulating or expressing LRP2 in one or more type of blood cell and culturing the cell with lactoferrin. The blood cells, sometimes called "source blood" useful herein include white blood cells, or blood fractions containing the same. Useful blood cells/sources also include cord blood cells, peripheral blood mononuclear cells (PMBC), hone marrow cells, whole blood, pluripotent stern cells, induced pluripotent stem cells, and multipotent stem cells. In one embodiment, the blood cells are a cell type or types which is/are isolated from one or more of the cell types/sources described herein. In one embodiment, the blood cells are PBMCs. In another embodiment, the cells are cord blood cells. In another embodiment, the cells are CD14+ cells. In another embodiment, the cells are monocytes. In another embodiment, the cells are granulocytes (or polymorphonuclear neutrophils, PMN). In yet another embodiment, the cells are CD34+ progenitor cells.

In some embodiments, the source blood cells endogenously express LRP2. Such cells include umbilical cord blood cells. In other embodiments, the source blood cells do not endogenously express LRP2. Blood cells which do not endogenously express LRP2 are treated or modified to activate or express LRP2.

The blood cells may, in one embodiment, be derived from the same subject to which they will ultimately be administered (i.e., an autologous transfusion). In another embodiment, the source of the blood cells is a donor or donors.

In one embodiment, the MDSCs may be generated ex vivo. As used herein, ex vivo refers to a procedure in which an organ, cells, or tissue are taken from a living body for treatment or procedure, and then returned to the (same or different) living body.

In one embodiment, the first step of the MDSC generation process involves isolation of the source blood. In one embodiment, PMN cells are isolated or enriched from the source blood. Techniques for isolating PMN from whole blood or other sources are known in the art. In one embodiment, PMN are isolated using negative selection with magnetic beads (Fan et al, Interrogating Parkinson's disease LRRK2 kinase pathway activity by assessing Rab10 phosphorylation in human neutrophils. Biochem J. 2018 Jan. 15; 475(1): 23-44 (online publication Nov 2017), which is incorporated by reference herein. In another embodiment, PMN are isolated using a density gradient (Oh et al. Neutrophil Isolation Protocol. J Vis Exp. 2008; (17): 745 (July 2008), Kuhns et al, Isolation and Functional Analysis of Human Neutrophils, Curr Protoc Immunol. Nov 2015: 111: 7.231-7.23.16, both of which are incorporated herein by reference). In one embodiment, PMN are isolated from cord blood (CB) of healthy individuals using negative selection with magnetic beads.

In another embodiment, monocytes (MON) are isolated or enriched. Monocytes can be isolated using techniques known in the art, including isolation of CD14+ cells from PBMC using magnetic beads (Heideveld et al, CD14+ cells from peripheral blood positively regulate hematopoietic stem and progenitor cell survival resulting in increased erythroid yield, Haematologica. 2015 November; 100(11): 1396-1406) and density gradients (Repnik et al, Simple and cost-effective isolation of monocytes from buffy coats, J Immunol Methods. 2003 July; 278(1-2):283-92). Both of these references are incorporated herein.

In another embodiment, CD34+ progenitor cells are isolated or enriched from the source blood. CD34+ progenitors can be isolated using techniques known in the art, including isolation of CD34+ cells from mononuclear cells from human bone marrow, peripheral blood or cord blood using magnetic beads (handle et al, Infection of human CD34+ progenitor cells with Bartonella henselae results in intraerythrocytic presence of B. henselae, Blood. 2005 Aug. 15; 106(4):1215-22. Epub 2005 Apr. 28, which is incorporated herein by reference).

In one embodiment, PMN and/or MON are generated from CD34+ progenitors using techniques known in the art. Such techniques include culture with one or more cytokines. Such cytokines include granulocyte-macrophage colony-stimulating factor (GM-CSF), granulocyte: colony-stimulating factor (G-CSF), flt-3 ligand (Flt3-L), stem cell factor (SCF), interleukin 3 (IL-3), interleukin 6 (IL-6), fetal bovine serum (FBS) and thrombopoietin (TPO). Concentrations of cytokines may be established based on culture conditions, but may range from about 5 ng/mL to about 500 ng/mL, including endpoints and all numbers therebetween. Cytokine concentrations may include 5 ng/mL, 10 ng/mL, 15 ng/mL, 20 ng/mL, 25 ng/mL, 30 ng/mL, 35 ng/mL, 40 ng/mL, 45 ng/mL, 50 ng/mL, 55 ng/mL, 60 ng/mL, 65 ng/mL, 70 ng/mL, 75 ng/mL, 80 ng/mL, 85 ng/mL, 90 ng/mL, 95 ng/mL, 100 ng/mL, 105 ng/mL, 110 ng/mL, 115 ng/mL, 120 ng/mL, 125 ng/mL, 130 ng/mL, 135 ng/mL, 140 ng/mL, 145 ng/mL, 150 ng/mL, 155 ng/mL, 160 ng/mL, 165 ng/mL, 170 ng/mL, 175 ng/mL, 180 mg/mL, 185 ng/mL, 190 ng/mL, 195 ng/mL, 200 ng/mL, 205 ng/mL, 210 ng/mL, 215 mg/mL, 220 ng/mL, 225 ng/mL, 230 ng/mL, 235 ng/mL, 240 ng/mL, 245 ng/mL, 250 ng/mL, 255 ng/mL, 260 ng/mL, 265 ng/mL, 270 ng/mL, 275 ng/mL, 280 ng/mL, 285 ng/mL, 290 ng/mL, 295 ng/mL, 300 ng/mL, 305 ng/mL, 310 ng/mL, 315 ng/mL, 320 ng/mL, 325 ng/mL, 330 ng/mL, 335 ng/mL, 340 ng/mL, 345 mg/mL, 350 ng/mL, 355 ng/mL, 360 ng/mL, 365 ng/mL, 370 ng/mL, 375 ng/mL, 380 ng/mL, 385 ng/mL, 390 ng/mL, 395 ng/mL, 400 ng/mL, 405 ng/mL, 410 ng/mL, 415 ng/mL, 420 ng/mL, 425 ng/mL, 430 ng/mL, 435 ng/mL, 440 ng/mL, 445 ng/mL, 450 ng/mL, 455 ng/mL, 460 ng/mL, 465 ng/mL, 470 ng/mL, 475 ng/mL, 480 ng/mL, 485 ng/mL, 490 ng/mL, 495 ng/mL, and 500 ng/mL.

The cells are cultured for the desired amount of time. In one embodiment, the cells are cultured for 1 day to 14 days. In another embodiment, the cells are cultured for 2, 3, 4, 5, 6, 7, 8, 9, 10, 11, 12, 13 or 14 days, or any time therebetween.

In one embodiment, PMN and MON are generated from CD34+ cells using 9-day culture with GM-CSF and G-CSF on the monolayer of OP9 feeder cells. See Jie et al, Large-scale ex vivo generation of human neutrophils from cord blood CD34-F cells, PLoS One. July 2017; 12(7): e0180832, Which is incorporated herein by reference. In one embodiment, the PMN and MON are cultured with one or more cytokines (as described above) to protect viability. In one embodiment, the cytokine includes GM-CSF.

The method includes in some embodiments, upregulating or expressing LRP2 in blood cells. In some embodiments, the source blood cells endogenously express LRP2. However, the source blood cells need not express LRP2 endogenously. The blood cells may be modified to express or treated to activate expression of LRP2.

For example, a nucleic acid encoding LRP2 can be packaged into or on the surface of delivery vehicles for delivery to cells. Delivery vehicles contemplated include, but are not limited to, nanospheres, liposomes, quantum dots, nanoparticles, polyethylene glycol particles, hydrogels, and micelles. As described in the art, a variety of targeting moieties can be used to enhance the preferential interaction of such vehicles with desired cell types or locations.

Introduction of LRP2 encoding nucleic acids into cells can occur by viral or bacteriophage infection, transfection, conjugation, protoplast fusion, lipofection, electroporation, nucleofection, calcium phosphate precipitation, polyethyleneimine (PED-mediated transfection, DEAE-dextran mediated transfection, liposome-mediated transfection, particle gun technology, calcium phosphate precipitation, direct micro-injection, nanoparticle-mediated nucleic acid delivery, and the like. Such techniques are known in the art. For example, in one embodiment, the source blood cells may be modified to introduce a recombinant nucleic acid sequence which encodes LRP2 or a functional fragment thereof. In addition, source blood which endogenously expresses LRP2 may be modified to introduce a recombinant nucleic acid sequence which encodes LRP2 or a functional fragment thereof to enhance or overexpress the receptor. Thus, in one embodiment, the method includes introducing to the blood cell a recombinant nucleic acid sequence which encodes LRP2 or a functional fragment thereof. Techniques for introducing such nucleic acids into blood cells are known in the art. In one embodiment, the method includes transducing the blood cells with a viral vector which comprises a LRP2 coding sequence. In one embodiment, the viral vector is a lentiviral vector. See. e.g., Mühlebach et al, Stable transduction of primary human monocytes by simian lentiviral vector PBj, Mol Ther. 2005 December; 12(6):1206-16. Epub 2005 Sep. 16, which is incorporated herein by reference.

In one embodiment, the cells are cultured with an LRP2 agonist. Various LRP2 agonists are known in the art and are useful herein. In one embodiment, the LRP2 agonist is PPARα/γ or an agonist thereof. In one embodiment, the PPARα/γ agonist is fenofibrate. In another embodiment, the PPARα/γ agonist is gemfibrozil. In another embodiment, the PPARα/γ agonist is pioglitazone. In another embodiment, the PPARα/γ agonist is rosiglitazone. In another embodiment, the PPARα/γ agonist is telmisartan. In another embodiment, the PPARα/γ agonist is or WY 14643. In one embodiment, the LRP2 agonist is PPARγ agonist. In yet another embodiment, the PPARγ agonist is used in combination with one or more agent.

In one embodiment, the PPARγ agonist is roscovitine. In another embodiment, the PPARγ agonist is DBZ. In another embodiment, the PPARγ agonist is MIN-102 (Minoryx Therapeutics). In another embodiment, the PPARγ agonist is Efatutazone (CS-7017) (Daiichi Sankyo Co., ltd). In another embodiment, the PPARγ agonist is Lobeglitazone (Chong Kun Dang Pharmaceutical Corp). In another embodiment, the PPARγ agonist is BR-101549 acts as peroxisome proliferator-activated receptor (PPAR) gamma agonist (Borvung Pharmaceutical Co Ltd). In another embodiment, the PPARγ agonist is Troglitazone. In another embodiment, the PPARγ agonist is ADC-8316 (Pulmagen Therapeutics). In another embodiment, the PPARγ agonist is L-phenylglycine or a derivative thereof (Chengdu Di'ao Pharmaceutical Group Co Ltd). In another embodiment, the PPARγ agonist is Rosiglitazone maleate (GenPharma International). In another embodiment, the PPARγ agonist is Rosuvastatin (Wallace Pharmaceuticals).

In one embodiment, the LRP2 agonist is albumin. In one embodiment, the LRP2 agonist is Angiotensin II. In one embodiment, the LRP2 agonist is Angiotensin 1-7. In one embodiment, the LRP2 agonist is ApoB. In one embodiment, the LRP2 agonist is ApoE. In one embodiment, the LRP2 agonist is ApoH. In one embodiment, the LRP2 agonist is Apoj (Clusterin). In one embodiment, the LRP2 agonist is ApoM. In one embodiment, the LRP2 agonist is Aprotinin. In one embodiment, the LRP2 agonist is Bone morphogenetic protein 4. In one embodiment. the LRP2 agonist is Ca2+. In one embodiment, the LRP2 agonist is Cathepsin b. In one embodiment, the LRP2 agonist is Coagulation Factor VIII. In one embodiment, the LRP2 agonist is Connective tissue growth factor. In one embodiment, the LRP2 agonist is Cytochrome C. In one embodiment, the LRP2 agonist is Cystatin C. In one embodiment, the LRP2 agonist is Epidermal growth factor. In one embodiment, the LRP2 agonist is Folate binding protein. In one embodiment, the LRP2 agonist is Hemoglobin. In one embodiment, the LRP2 agonist is Insulin. In one embodiment, the LRP2 agonist is Leptin. In one embodiment, the LRP2 agonist is Lipoprotein lipase. In one embodiment, the LRP2 agonist is Metallothionein. In one embodiment, the LRP2 agonist is Plasminogen. In one embodiment, the LRP2 agonist is Plasminogen activator inhibitory type 1. In one embodiment, the LRP2 agonist is Plasminogen activator inhibitory type 1 urokinase. In one embodiment, the LRP2 agonist is Plasminogen activator inhibitory type 1 tissue plasminoegen activator. In one embodiment, the LRP2 agonist is Retinol binding protein. In one embodiment, the LRP2 agonist is Sonic hedgehog protein. In one embodiment, the LRP2 agonist is Aminoglycosides. In one embodiment, the LRP2 agonist is α-Amilase. In one embodiment, the LRP2 agonist is α-galactosidase. In one embodiment, the LRP2 agonist is Gelsolin. In one embodiment, the LRP2 agonist is Insulin Growth factor I. In one embodiment, the LRP2 agonist is Liver type fatty acid binding protein. In one embodiment, the LRP2 agonist is Lysozyme. In one embodiment, the LRP2 agonist is Microglobulin. In one embodiment, the LRP2 agonist is Myoglobulin. In one embodiment, the LRP2 agonist is Neutrophil gelatinase associated lipocalin. In one embodiment, the LRP2 agonist is Odorant binding protein. In one embodiment, the LRP2 agonist is Parathyroid hormone. In one embodiment, the LRP2 agonist is Pancreatitis associated protein 1. In one embodiment, the LRP2 agonist is Polymyxin B. In one embodiment, the LRP2 agonist is Prolactin. In one embodiment, the LRP2 agonist is Pro Urokinase. In one embodiment, the LRP2 agonist is Seleno protein P. In one embodiment, the LRP2 agonist is Seminal vesicle secretory protein II. In one embodiment, the LRP2 agonist is Sex hormone binding globulin. In one embodiment, the LRP2 agonist is Thyroglobulin. In one embodiment, the LRP2 agonist is Transcobalamin vitamin B12. In one embodiment, the LRP2 agonist is Transthyretin. In one embodiment, the LRP2 agonist is Trichosantin. In one embodiment, the LRP2 agonist is Vitamin D binding protein.

In another embodiment, the LRP2 agonist is selected from Table 2.

TABLE 2

LRP2 Agonists

| Receptor | Ligand | Reference |
| --- | --- | --- |
| LRP1 and LRP2 | Albumin | Cui et al., 1996 |
| LRP1 and LRP2 | Angiotensin II | Gonzalez-Villalobos et al., 2005 |
| LRP1 and LRP2 | Angiotensin 1-7 | Gonzalez-Villalobos et al., 2006 |
| LRP1 and LRP2 | ApoB | Stefansson et al., 1995 |
| LRP1 and LRP2 | ApoE | Willnow, 1999 |
| LRP1 and LRP2 | ApoH | Moestrup and Verroust, 2001 |
| LRP1 and LRP2 | Apoj (Clusterin) | Kounnas et al., 1995; Hammad et al., 1997 |
| LRP1 and LRP2 | ApoM | Faber et al., 2006 |
| LRP1 and LRP2 | Aprotinin | Moestrup and Verroust, 2001 |
| LRP1 and LRP2 | Bone morphogenetic protein 4 | Spoelgen et al., 2005 |
| LRP1 and LRP2 | Ca2+ | Christensen and Nielsen, 2007 |
| LRP1 and LRP2 | Cathepsin b | Nielsen et al., 2007 |
| LRP1 and LRP2 | Coagulation Factor VIII | Ananyeva et al., 2008 |
| LRP1 and LRP2 | Connective tissue growth factor | Gerritsen et al., 2010; Kawata et al., 2012 |
| LRP1 and LRP2 | Cytochrome C | Lee et al., 2012 |
| LRP1 and LRP2 | Cystatin C | Kaseda et al., 2007 |
| LRP1 and LRP2 | Epidermal growth factor | Orlando et al., 1998 |
| LRP1 and LRP2 | Folate binding protein | Birn et al., 2005 |
| LRP1 and LRP2 | Hemoglobin | Gburek et al., 2002 |
| LRP1 and LRP2 | Insulin | Orlando et al., 1998 |
| LRP1 and LRP2 | Lactoferrin | Willnow, 1999 |
| LRP1 and LRP2 | Leptin | Dietrich et al., 2008 |
| LRP1 and LRP2 | Lipoprotein lipase | Kounnas et al., 1993 |
| LRP1 and LRP2 | Metallothionein | Klassen et al., 2004 |

TABLE 2-continued

LRP2 Agonists

| Receptor | Ligand | Reference |
| --- | --- | --- |
| LRP1 and LRP2 | Plasminogen | Kanalas and Makker, 1993 |
| LRP1 and LRP2 | Plasminogen activator inhibitory type 1 | Stefansson et al., 1995 |
| LRP1 and LRP2 | Plasminogen activator inhibitory type 1 urokinase | Moestrup and Verroust, 2001 |
| LRP1 and LRP2 | Plasminogen activator inhibitory type 1 tissue plasminoegen activator | Kanalas and Hopfer, 1997; Moestrup and Verroust, 2001 |
| LRP1 and LRP2 | Retinol binding protein | Christensen and Nielsen, 2007 |
| LRP1 and LRP2 | Sonic hedgehog protein | Christ et al., 2012 |
| LRP2 | Aminoglycosides | Moestrup and Verroust, 2001 |
| LRP2 | α-Amilase | Birn et al., 2000 |
| LRP2 | α-galactosidase | Christensen and Nielsen, 2007 |
| LRP2 | Gelsolin | Vargas et al., 2010a |
| LRP2 | Insulin Growth factor I | Carro et al., 2002 |
| LRP2 | Liver type fatty-acid binding protein | Oyama et al., 2005 |
| LRP2 | Lysozyme | Orlando et al., 1998 |
| LRP2 | Microglobulin | Leheste et al., 1999 |
| LRP2 | Myoglobulin | Gburek et al., 2002 |
| LRP2 | Neutrophil gelatinase associated lipocalin | Hvidberg et al., 2005 |
| LRP2 | Odorant binding protein | Leheste et al., 1999 |
| LRP2 | Parathyroid hormone | Hilpert et al., 1999 |
| LRP2 | Pancreatitis associated protein 1 | Leheste et al., 1999 |
| LRP2 | Polymyxin B | Moestrup and Verroust, 2001 |
| LRP2 | Prolactin | Orlando et al., 1998 |
| LRP2 | Pro Urokinase | Stefansson et al., 1995 |
| LRP2 | Seleno protein P | Olson et al., 2008 |
| LRP2 | Seminal vesicle secretory protein II | Ranganathan et al., 1999 |
| LRP2 | Sex hormone binding globulin | Hammes et al., 2005 |
| LRP2 | Thyroglobulin | Zheng et al., 1998 |
| LRP2 | Transcobalamin vitamin B12 | Moestrup and Verroust, 2001 |
| LRP2 | Transthyretin | Sousa et al., 2000 |
| LRP2 | Trichosantin | Chan et al., 2000 |
| LRP2 | Vitamin D binding protein | Nykjaer et al., 1999 |

Each of these references is incorporated herein by reference in its entirety.

In one embodiment, the cells are cultured with the LRP2 agonist in an amount ranging from about 0.01 mg/ml to about 10 mg/ml, including all amounts therebetween and end points. In one embodiment, the LRP2 agonist concentration is about 0.1 mg/ml to about 5 mg/ml, including all amounts therebetween and end points. In another embodiment, the LRP2 agonist concentration is about 0.3 mg/ml to about 1.0 mg/ml, including all amounts therebetween and end points. In another embodiment, the LRP2 agonist concentration is about 0.3 mg/ml. In another embodiment, the LRP2 agonist concentration is about 0.4 mg/ml. In another embodiment, the LRP2 agonist concentration is about 0.5 mg/ml. In another embodiment, the LRP2 agonist concentration is about 0.6 mg/ml. In another embodiment, the LRP2 agonist concentration is about 0.7 mg/ml. In another embodiment, the LRP2 agonist concentration is about 0.8 mg/ml. In another embodiment, the LRP2 agonist concentration is about 0.9 mg/ml. In another embodiment, the LRP2 agonist concentration is about 1.0 mg/ml.

In one embodiment, the cells are cultured with the LRP2 agonist in an amount ranging from about 1 µM to about 2 mM, including all amounts therebetween and end points. In one embodiment, the LRP2 agonist concentration is about 10 µM to about 100 µM, including all amounts therebetween and end points. In another embodiment, the LRP2 agonist concentration is about 5 µM. In another embodiment, the LRP2 agonist concentration is about 10 µM. In another embodiment, the LRP2 agonist concentration is about 20 µM. In another embodiment, the LRP2 agonist concentration is about 50 uM. In another embodiment, the LRP2 agonist concentration is about 100 µM. In another embodiment, the LRP2 agonist concentration is about 200 µM. In another embodiment, the LRP2 agonist concentration is about 300 µM. In another embodiment, the LRP2 agonist concentration is about 400 µM. In another embodiment, the LRP2 agonist concentration is about 500 µM. In another embodiment, the LRP2 agonist concentration is about 600 µM. In another embodiment, the LRP2 agonist concentration is about 700 µM. In another embodiment, the LRP2 agonist concentration is about 800 µM. In another embodiment, the LRP2 agonist concentration is about 900 µM. In another embodiment, the LRP2 agonist concentration is about 1 mM. In another embodiment, the LRP2 agonist concentration is about 1,25 mM. In another embodiment, the LRP2 agonist concentration is about 1.5 mM. In another embodiment, the LRP2 agonist concentration is about 1.75 mM. In another embodiment, the LRP2 agonist concentration is about 2 mM.

The cells are cultured with an LRP2 agonist for a time sufficient to generate MDSCs. In one embodiment, the cells are cultured with the LRP2 agonist for about 1 hour to about 48 hours. In another embodiment, cells are cultured for 2, 3, 4, 5, 6, 7, 8, 9, 10, 11, 12, 13, 14, 15, 16, 17, 18, 19, 20, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, or 72 hours. In one embodiment, cells are collected after 6, 12, 24, and 48 hrs.

In another embodiment, the cells are cultured with lactoferrin. The lactoferrin may be any lactoferrin compound as described herein, including those shown in Table 1. In one embodiment, the lactoferrin is a lactoferrin related peptide as described in U.S. Pat. No. 7,420,033, which is incorporated herein by reference.

The cells are cultured with lactoferrin in an amount ranging from about 0.01 mg/ml to about 10 mg/ml, including all amounts therebetween and end points. In one embodiment, the LF concentration is about 0.1 mg/ml to about 5 mg/ml, including all amounts therebetween and end points. In another embodiment, the LF concentration is about 0.3 mg/ml to about 1.0 mg/ml, including all amounts therebetween and end points. In another embodiment, the LF concentration is about 0.3 mg/ml. In another embodiment, the LF concentration is about 0.4 mg/ml. In another embodiment, the LF concentration is about 0.5 mg/ml. In another embodiment, the LF concentration is about 0.6 mg/ml. In another embodiment, the LF concentration is about 0.7 mg/ml. In another embodiment, the LF concentration is about 0.8 mg/ml. In another embodiment, the LF concentration is about 0.9 mg /ml. In another embodiment, the LF concentration is about 1.0 mg/ml.

The cells are cultured with lactoferrin for a time sufficient to generate MDSCs. In one embodiment, the cells are cultured with LF for about 1 hour to about 72 hours. In another embodiment, cells are cultured for 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, or 72 hours. In one embodiment, cells are collected after 6, 12, 24, and 48 hrs.

In one embodiment, the cells are cultured with lactoferrin at the same time as being treated with an LRP2 agonist. In another embodiment, the cells are cultured with lactoferrin before being treated with an LRP2 agonist. In another embodiment, the cells are cultured with lactoferrin after being treated with an LRP2 agonist.

Viability of the cells is assessed via known techniques (e.g., trypan blue staining). In one embodiment, the cells are further tested if viability is above a certain threshold. In one embodiment, viability is above 50%, 55%, 60%, 70%, 75%, 80%, 85%, 90%, or 95%. In a preferred embodiment, if viability is at or above 75%, cells are tested further to determine whether they meet the characterization criteria for MDSC. Such tests include those described by Bronte et al, Recommendations for myeloid-derived suppressor cell nomenclature and characterization standards, Nat Commun. 2016; 7: 12150, which is incorporated herein by reference.

In some embodiments, phenotypic studies are performed. As noted above, MDSC may fall into one of the following subpopulations: PMN-MDSC ($CD11b^+Ly6G^+Ly6C^{lo}$) and M-MDSC ($CD11b^+Ly6G^-Ly6C^{hi}$). In human peripheral blood mononuclear cell (PBMC), the equivalent to PMN-MDSC are defined as $CD11^+CD14^-CD15^+$ or $CD11b^+CD14^-CD66b^+$ and M-MDSC as $CD11b^+CD14^+HLA-DR^{-/lo}CD15^-$. CD33 myeloid marker can be used instead of CD11b since very few $CD15^+$ cells are $CD11b^-$. While M-MDSC express the myeloid marker CD33, PMN-MDSC display $CD33^{dim}$ staining. $Lin^-$ (including CD3, CD14, CD15, CD19, CD56) $HLA-DR^-CD33^+$ cells contain mixed groups of MDSC comprising more immature progenitors. These cells have been defined as early-stage iMDSC (eMDSC).

In some embodiments, the cells are tested in a T cell suppression assay to assess MDSC suppressive activity. Such assays are known in the art, and are described herein. In brief, sorted $CD3^+$ T cells from the spleen are labeled with CFSE, stimulated with anti-CD3-coated plates and soluble anti-CD28, and cultured alone or with M-MDSCs at different ratios for 3 d. Cells are then stained with anti-CD4-PE-Cy5 and anti-CD8a-PE, and I-cell proliferation is analyzed by flow cytometry. See, He et al, Nat Med. 2018 February; 24(2):224-231. doi: 10.1038./nm.4467. Epub 2018 Jan. 15, which is incorporated herein by reference in its entirety.

Other methods of assessing MDSC activity include inhibition of 3H-thymidine incorporation or CFSE dilution; inhibition of cytotoxic T lymphocyte activity; inhibition of IFN-γ production by T cells in ELISPOT or intracellular staining; inhibition of expression of CD3ζ chain on cells; inhibition of IL-2 production; inhibition of anti-CD3/CD28 (or PHA) induced T-cell proliferation or IFN-γ production (in ELISPOT or by intracellular staining) by the addition of candidate MDSC populations; and improved T-cell proliferation after removal of candidate MDSC populations. See Bronte et al,cited above.

In another embodiment, the cells are tested to see if they induce anti-bacterial activity by evaluating phagocytosis and cytotoxicity against *E. coli* and *C. albicans*. Assays to evaluate phagocytosis and cytotoxicity against bacteria. See, e.g., Hofman et al, Increased *Escherichia coli* Phagocytosis in Neutrophils That Have Transmigrated across a Cultured Intestinal Epithelium, Infect Immun. 2000 February; 68(2): 449-455 and Li et al, A critical concentration of neutrophils is required for effective bacterial killing in suspension. PNAS June 11, 2002 99 (12) 8289-8294, which are incorporated herein by reference.

In another embodiment, the cells are subjected to an allogeneic mixed leukocyte reaction (MLR) to assess functional activity in one embodiment, a three-way allogeneic MLR is performed. This assay utilizes cells obtained from a pair of unrelated healthy donors: one is the source of T cells, the other one provides APCs. The pair is selected based on strong T-cell proliferative or IFN-γ responses of the responder, and aliquots of cells can be stored for use in subsequent iterative experiments. MDSCs from cancer patients are tested in MLR at different ratios compared with responder T cells. The assay is based on the premise that allogeneic MLR requires presentation of epitopes in the context of WIC class II and class I, so that suppression of responses reflects the ability of MDSC to prevent antigen-specific T-cell immune responses. In one embodiment, as a control, cells are incubated without LF.

Pharmaceutical Compositions and Administration

In one aspect, provided are pharmaceutical compositions which include MDSC generated according to the methods described herein for treatment of an inflammatory condition or disease. Such pharmaceutical compositions may include pharmaceutically acceptable carriers, The pharmaceutical compositions and MDSCs described herein are useful in cell therapies, both autologous and allogeneic. Autologous cell therapy (ACT) is a therapeutic intervention that uses an individual's cells, which are cultured and expanded outside the body, and reintroduced into the donor, while allogeneic therapy uses cells from a genetically different donor. Advantages of the autologous approach include the minimization of risks from systemic immunological reactions, bio-incompatibility, and disease transmission associated with grafts or cells not cultivated from the individual. In one embodiment, the methods include removal of the source blood cells from the donor. The donor may be the same subject or a different subject than the ultimate recipient of the MDSCs.

In one aspect, a method of treating an inflammatory disease in a subject is provided. The method includes administering a therapeutically effective amount of a pharmaceutical composition comprising MDSCs as generated herein. In one embodiment, the therapeutically effective amount is about $1\times10^5$ to about $1\times10^{14}$ cells, preferably $1\times10^8$ to $1\times10^{11}$ cells, including endpoints and all integers therebetween. In another embodiment, the effective amount is about $5\times10^8$ to $2\times10^{10}$ cells, including endpoints and all integers therebetween.

In another aspect, a method of reducing the likelihood of occurrence or severity of an inflammatory disease in a subject is provided. The method includes administering a therapeutically effective amount of a pharmaceutical composition comprising MDSCs as generated herein.

In one embodiment of these methods, the subject is a child. In another embodiment, the subject is a neonate. In another embodiment, the subject is a neonate having or at risk for necrotizing enterocolitis. In another embodiment, the subject is an adult having an autoimmune disease. In another embodiment, the subject is an older adult having, or at risk for, an autoimmune disease.

In one aspect, a therapeutically effective amount of MDSCs as generated according to a method described herein, are provided for use in treating an inflammatory disease in a subject. In yet another embodiment, the MDSCs are provided in conjunction with another therapy. In one embodiment, the additional therapy is a corticosteroid.

In another aspect, use of a composition comprising MDSCs as generated herein is provided for reducing the likelihood of occurrence or severity of an inflammatory disease in a subject.

Dosages and administration regimen can be adjusted depending on the age, sex, physical condition of administered as well as the benefit of the conjugate and side effects in the patient or mammalian subject to be treated and the judgment of the physician, as is appreciated by those skilled in the art.

Unless defined otherwise in this specification, technical and scientific terms used herein have the same meaning as commonly understood by one of ordinary skill in the art and by reference to published texts, which provide one skilled in the art with a general guide to many of the terms used in the present application.

The following examples are illustrative only and are not intended to limit the present invention.

EXAMPLES

Example 1

Bone marrow cells were treated overnight with 2 micromolar Rosiglitazone and 700 microgram/ml lactoferrin. Cells were washed and used for experiments. FIG. 1 shows LRP2 expression on Ly6G+-neutrophils (right) and Ly6C-+-monocytes (left) from spleen measured before and after rosiglitazone (2 uM) treatment for 2 hours. LRP2 expression in treated neutrophils, and to a lesser extent monocytes, was increased in rosiglitazone treated cells.

Figure 2:
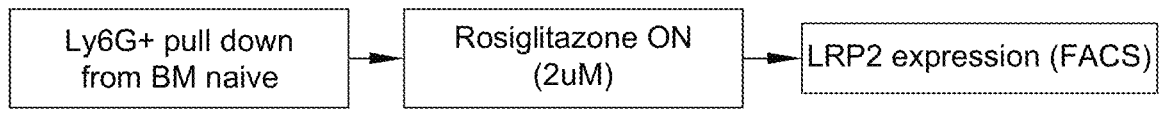
FIG. 2 shows LRP2 expression on Ly6G+-neutrophils from bone marrow measured after rosiglitazone (2 uM) treatment. LRP2 expression in treated neutrophils was increased in rosiglitazone treated cells, FIGS. 3A and 3B demonstrate the effect of Lrp2 overexpression on myeloid cell response to LF.
Figure 2:
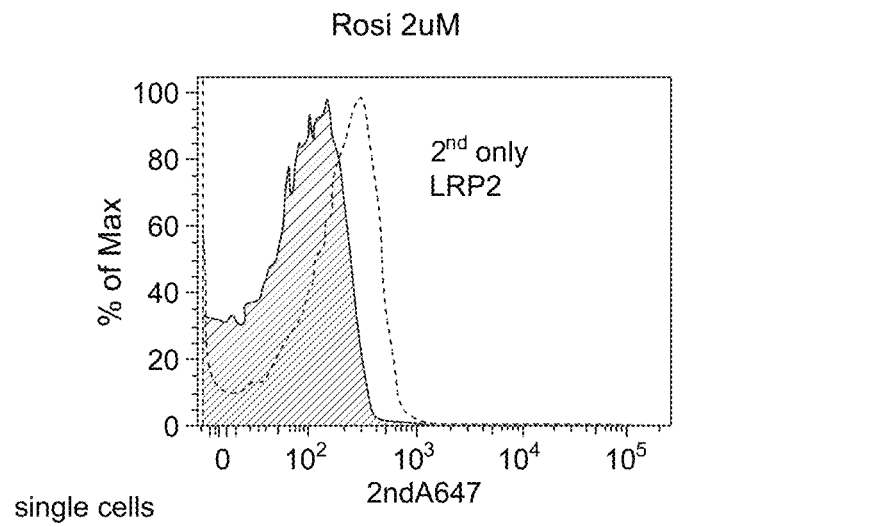
Figure 2:
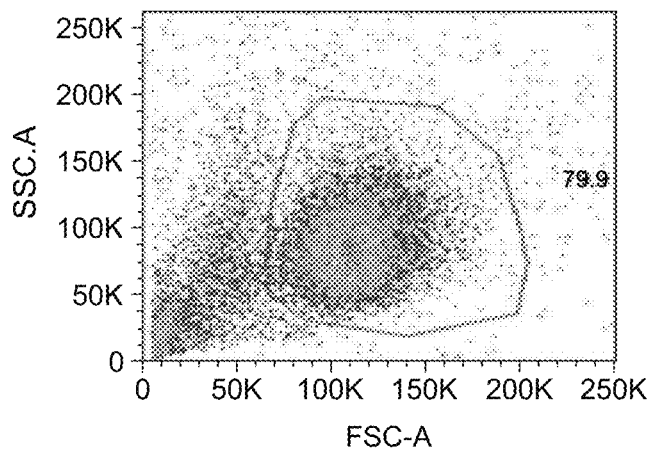

FIG. 2 shows LRP2 expression on Ly6G+-neutrophils from bone marrow measured after rosiglitazone (2 uM) treatment. LRP2 expression in treated neutrophils was increased in rosiglitazone treated cells.

Figure 3A:
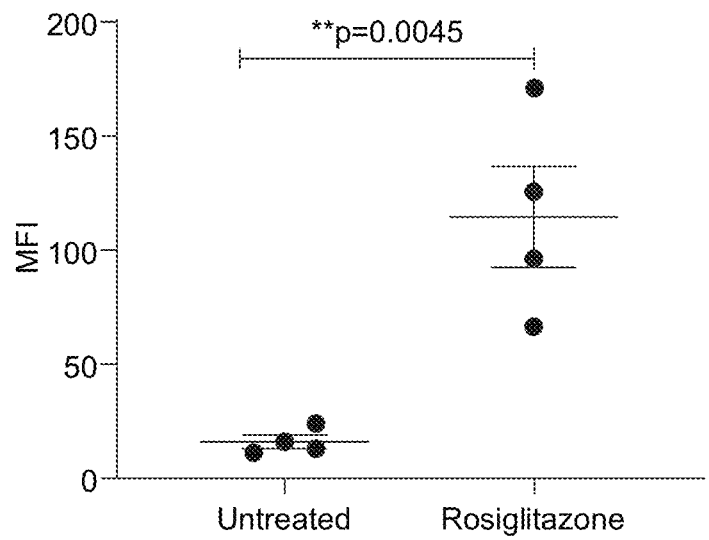
FIG. 3A. BM cells from adult mice were treated with 2 mM Rosiglitazone and Lrp2 expression in CD11b+Ly6CloLy6G+ PMN was measured (n=4).

BM cells from adult mice were treated with 2M Rosiglitazone and Lrp2 expression in CD11b+Ly6CloLy6G+ PMN was measured (n=4). FIG. 3A demonstrates increased expression of LRP2 in treated cells.

Figure 3B:
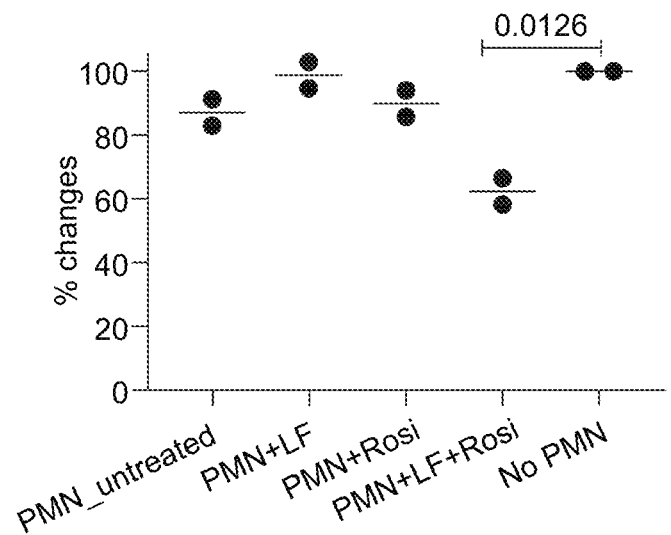
FIG. 3B. PMN were treated with 2 mM Rosiglitazone and 700 ug/ml LF overnight and then used to suppress response of OT-1 splenocytes to cognate peptide. Percentage of change of proliferation from no PMN group is shown.

PMN were treated with 2 mM Rosiglitazone and 700 ug/ml LF overnight and then used to suppress response of OT-1 splenocytes to cognate peptide (FIG. 3B). Percentage of change of proliferation from no PMN group is shown. PMN cells treated with LF and Rosiglitazone show a decrease in response of splenocytes as compared to LF or Rosiglitazone alone or controls.

All publications cited in this specification, as well as U.S. Provisional Patent Application No. 62/869,922, are incorporated herein by reference. While the invention has been described with reference to particular embodiments, it will be appreciated that modifications can be made without departing from the spirit of the invention. Such modifications are intended to fall within the scope of the appended claims.

What is claimed is:

1. A method of generating Myeloid-derived suppressor cells (MDSCs) ex vivo, the method comprising upregulating or expressing LRP2 in blood cells by culturing said blood cells with an LRP2 agonist and culturing said cells with lactoferrin, thereby generating MDSCs wherein the LRP2 agonist is PPARα, PPARγ, or an agonist of PPARα or PPARγ and the blood cells comprise white blood cells, cord blood cells, peripheral blood mononuclear cells (PMBC), bone marrow cells, whole blood, CD14+ cells, monocytes, granulocytes, polymorphonuclear neutrophils (PMN), or CD34+ cells.

2. The method of claim 1, wherein the blood cells are selected from peripheral blood mononuclear cells, cord blood, or bone marrow cells.

3. The method of claim 1, wherein the LRP2 agonist is fenofibrate, gemfibrozil, pioglitazone, rosiglitazone, telmisartan, WY 14643, roscovitine, DBZ, MIN-102, Efatutazone (CS-7017), Lobeglitazone, BR-101549, Troglitazone, ADC-8316, L-phenylglycine, Rosiglitazone maleate, or Rosuvastatin.

4. The method of claims 1, wherein the culture medium further comprises GM-CSF, IL-6 or both.

5. The method of claim 1, further comprising transducing the blood cells with a viral vector which comprises a LRP2 coding sequence.

6. The method of claim 5, wherein the viral vector is a lentiviral vector.

7. The method of claim 1, wherein said MDSCs have the phenotype of CD11b+CD14-CD15+, CD11b+CD14-CD66b+, or CD11b+CD14+HLA-DR-/loCD15-.

8. The method of claim 1, further comprising removing said blood cells from a subject prior to culturing said cells.

9. The method of claim 8, further comprising isolating PBMCs from whole blood prior to culturing said PBMCs.

10. The method of claim 1, further comprising isolating or enriching CD34+ cells.

11. The method of claim 1, further comprising isolating or enriching PMN.

12. The method of claim 1, further comprising culturing CD34+progenitors to generate PMN and/or monocytes.

13. The method of claim 1, further comprising assaying the blood cells for MDSC phenotype, morphology, or activity.

* * * * *